US010590191B2

(12) United States Patent
Fagret et al.

(10) Patent No.: US 10,590,191 B2
(45) Date of Patent: Mar. 17, 2020

(54) ANTI-TAU NANOBODIES

(71) Applicants: UNIVERSITE GRENOBLE ALPES, Saint Martin d'Heres (FR); CENTRE HOSPITALIER UNIVERSITAIRE GRENOBLE ALPES, La Tronche (FR); INSTITUT NATIONAL DE LA SANTE ET DE LA RECHERCHE MEDICALE (INSERM), Paris (FR)

(72) Inventors: Daniel Fagret, La Tronche (FR); Marcelle Moulin, La Tronche (FR); Catherine Ghezzi, La Tronche (FR); Pascale Perret, La Tronche (FR); Sabine Chierici, Grenoble (FR)

(73) Assignees: UNIVERSITE GRENOBLE ALPES, Saint Martin d'Heres (FR); CENTRE HOSPITALIER UNIVERSITAIRE GRENOBLE ALPES, La Tronche (FR); INSTITUT NATIONAL DE LA SANTE ET DE LA RECHERCHE MEDICALE (INSERM), Paris (FR)

(*) Notice: Subject to any disclaimer, the term of this patent is extended or adjusted under 35 U.S.C. 154(b) by 0 days.

(21) Appl. No.: 16/345,279

(22) PCT Filed: Oct. 27, 2017

(86) PCT No.: PCT/EP2017/077691
§ 371 (c)(1),
(2) Date: Apr. 26, 2019

(87) PCT Pub. No.: WO2018/078140
PCT Pub. Date: May 3, 2018

(65) Prior Publication Data
US 2019/0263898 A1 Aug. 29, 2019

(30) Foreign Application Priority Data

Oct. 27, 2016 (FR) ..................... 16 60450

(51) Int. Cl.
*C07K 16/18* (2006.01)
*A61P 25/28* (2006.01)
*C12N 15/86* (2006.01)
*A61K 39/00* (2006.01)

(52) U.S. Cl.
CPC .............. *C07K 16/18* (2013.01); *A61K 39/00* (2013.01); *A61P 25/28* (2018.01); *C12N 15/86* (2013.01); *C07K 2317/22* (2013.01); *C07K 2317/569* (2013.01); *C07K 2317/92* (2013.01)

(58) Field of Classification Search
None
See application file for complete search history.

(56) References Cited

U.S. PATENT DOCUMENTS

| 4,861,719 | A | 8/1989 | Miller |
| 5,278,056 | A | 1/1994 | Bank |
| 5,882,887 | A | 3/1999 | Noeske-Jungblut |
| 6,013,516 | A | 1/2000 | Verma |
| 2015/0266947 | A1 | 9/2015 | Sierks |

FOREIGN PATENT DOCUMENTS

| WO | 9419478 A1 | 9/1994 |
| WO | 9514785 A1 | 6/1995 |
| WO | 9622378 A1 | 7/1996 |
| WO | 2013041962 A1 | 3/2013 |
| WO | 2014059442 A2 | 4/2014 |

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*
Koenig "Mutational landscape of antibody variable domains reveals a switch modulating the interdomain conformational dynamics and antigen binding" PNAS E486-E495 (Year: 2017).*
Castillo-Carranza, Diana L. "Specific Targeting of Tau Oligomers in Htau Mice Prevents Cognitive Impairment and Tau Toxicity Following Injection with Brain-Derived Tau Oligomeric Seeds", Journal of Alzheimer's Disease, vol. 40, No. s1, May 17, 2014, pp. S97-S111.
Davidowitz, Eliot J. "Targeting tau oligomers for therapeutic development for Alzheimer's disease and taupathies", vol. 4, Jan. 1, 2008, pp. 47-64.
International Search Report for corresponding application PCT/EP2017/077691 filed Oct. 27, 2017; dated Jan. 19, 2018.
David, Monique Antoinette "Potential candidate camelid antibodies for the treatment of protein0misfolding diseases", Journal of Neuroimmunology, vol. 272, No. 1 Jul. 15, 2014, pp. 76-85.
Ferreira, Sergio T. "Soluble protein oligomers as emerging toxins in Alzheimer's and other amyloid diseases", IUBMB Life, vol. 59, No. 4, Jan. 1, 2004, pp. 332-345.

* cited by examiner

*Primary Examiner* — Adam Weidner
(74) *Attorney, Agent, or Firm* — Cantor Colburn LLP

(57) ABSTRACT

The invention relates to anti-Tau nanobodies.

17 Claims, 3 Drawing Sheets
Specification includes a Sequence Listing.

SEQUENCE LISTING

```
<160> NUMBER OF SEQ ID NOS: 27

<210> SEQ ID NO 1
<211> LENGTH: 8
<212> TYPE: PRT
<213> ORGANISM: Artificial Sequence
<220> FEATURE:
<223> OTHER INFORMATION: CDR1 consensus
<220> FEATURE:
<221> NAME/KEY: MISC_FEATURE
<222> LOCATION: (6)..(6)
<223> OTHER INFORMATION: Xaa is S or R
<220> FEATURE:
<221> NAME/KEY: MISC_FEATURE
<222> LOCATION: (7)..(7)
<223> OTHER INFORMATION: Xaa is D or Y
<220> FEATURE:
```

```
<221> NAME/KEY: MISC_FEATURE
<222> LOCATION: (8)..(8)
<223> OTHER INFORMATION: Xaa is T or A

<400> SEQUENCE: 1

Gly Arg Thr Phe Ser Xaa Xaa Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: CDR2 consensus
<220> FEATURE:
<221> NAME/KEY: MISC_FEATURE
<222> LOCATION: (3)..(3)
<223> OTHER INFORMATION: Xaa is P or R
<220> FEATURE:
<221> NAME/KEY: MISC_FEATURE
<222> LOCATION: (7)..(7)
<223> OTHER INFORMATION: Xaa is S or V

<400> SEQUENCE: 2

Ile Ser Xaa Ser Gly Gly Xaa Thr
1               5

<210> SEQ ID NO 3
<211> LENGTH: 8
<212> TYPE: PRT
<213> ORGANISM: Artificial Sequence
<220> FEATURE:
<223> OTHER INFORMATION: CDR1 of nanobody 2C5

<400> SEQUENCE: 3

Gly Arg Thr Phe Ser Ser Asp Thr
1               5

<210> SEQ ID NO 4
<211> LENGTH: 8
<212> TYPE: PRT
<213> ORGANISM: Artificial Sequence
<220> FEATURE:
<223> OTHER INFORMATION: CDR2 of nanobody 2C5

<400> SEQUENCE: 4

Ile Ser Pro Ser Gly Gly Val Thr
1               5

<210> SEQ ID NO 5
<211> LENGTH: 11
<212> TYPE: PRT
<213> ORGANISM: Artificial Sequence
<220> FEATURE:
<223> OTHER INFORMATION: CDR3 of nanobody 2C5

<400> SEQUENCE: 5

Asn Arg Asp Pro Lys Tyr Gly Asn Thr Arg Tyr
1               5                   10

<210> SEQ ID NO 6
<211> LENGTH: 8
<212> TYPE: PRT
<213> ORGANISM: Artificial Sequence
<220> FEATURE:
<223> OTHER INFORMATION: CDR1 of nanobody S2T2M3_E6

<400> SEQUENCE: 6
```

Gly Arg Thr Phe Ser Arg Tyr Ala
1               5

<210> SEQ ID NO 7
<211> LENGTH: 8
<212> TYPE: PRT
<213> ORGANISM: Artificial Sequence
<220> FEATURE:
<223> OTHER INFORMATION: CDR2 of nanobody S2T2M3_E6

<400> SEQUENCE: 7

Ile Ser Arg Ser Gly Gly Ser Thr
1               5

<210> SEQ ID NO 8
<211> LENGTH: 14
<212> TYPE: PRT
<213> ORGANISM: Artificial Sequence
<220> FEATURE:
<223> OTHER INFORMATION: CDR3 of nanobody S2T2M3_E6

<400> SEQUENCE: 8

Thr Ala Arg Arg Arg Ile Ser Gly Thr Pro Gln Trp His Tyr
1               5                   10

<210> SEQ ID NO 9
<211> LENGTH: 118
<212> TYPE: PRT
<213> ORGANISM: Artificial Sequence
<220> FEATURE:
<223> OTHER INFORMATION: variable region of nanobody 2C5

<400> SEQUENCE: 9

Gln Val Gln Leu Val Gln Ser Gly Gly Gly Leu Val Gln Ala Gly Gly
1               5                   10                  15

Ser Leu Arg Leu Ser Cys Ala Ala Ser Gly Arg Thr Phe Ser Ser Asp
            20                  25                  30

Thr Leu Ala Trp Phe Arg Gln Ala Pro Gly Lys Glu Arg Glu Phe Val
        35                  40                  45

Ala Ser Ile Ser Pro Ser Gly Gly Val Thr Tyr Tyr Glu Asp Ser Val
    50                  55                  60

Lys Gly Arg Phe Thr Ile Ser Arg Asp Asn Ser Lys Asn Thr Val Leu
65                  70                  75                  80

Leu Gln Met Asn Ser Leu Thr Pro Glu Asp Thr Ala Val Tyr Tyr Cys
                85                  90                  95

Asn Arg Asp Pro Lys Tyr Gly Asn Thr Arg Tyr Trp Gly Gln Gly Thr
            100                 105                 110

Gln Val Thr Val Ser Ser
        115

<210> SEQ ID NO 10
<211> LENGTH: 121
<212> TYPE: PRT
<213> ORGANISM: Artificial Sequence
<220> FEATURE:
<223> OTHER INFORMATION: variable region of nanobody S2T2M3_E6

<400> SEQUENCE: 10

Glu Val Gln Leu Val Glu Ser Gly Gly Gly Leu Val Gln Ala Gly Gly
1               5                   10                  15

Ser Leu Arg Leu Ser Cys Ala Ser Gly Arg Thr Phe Ser Arg Tyr
            20                  25                  30

Ala Met Gly Trp Phe Arg Gln Ala Pro Gly Lys Glu Arg Glu Phe Val
            35                  40                  45

Ala Ser Ile Ser Arg Ser Gly Gly Ser Thr Arg Tyr Ala Asp Ala Val
 50                  55                  60

Lys Gly Arg Phe Thr Ile Ser Arg Asp Asn Thr Asn Thr Val Tyr
 65                  70                  75                  80

Leu Leu Met Asn Asn Leu Lys Pro Glu Asp Thr Ala Val Tyr Tyr Cys
                 85                  90                  95

Thr Ala Arg Arg Arg Ile Ser Gly Thr Pro Gln Trp His Tyr Trp Gly
            100                 105                 110

Gln Gly Thr Gln Val Thr Val Ser Ser
        115                 120

<210> SEQ ID NO 11
<211> LENGTH: 25
<212> TYPE: PRT
<213> ORGANISM: Artificial Sequence
<220> FEATURE:
<223> OTHER INFORMATION: FR1 region of nanobody 2C5.

<400> SEQUENCE: 11

Gln Val Gln Leu Val Gln Ser Gly Gly Gly Leu Val Gln Ala Gly Gly
 1               5                  10                  15

Ser Leu Arg Leu Ser Cys Ala Ala Ser
             20                  25

<210> SEQ ID NO 12
<211> LENGTH: 17
<212> TYPE: PRT
<213> ORGANISM: Artificial Sequence
<220> FEATURE:
<223> OTHER INFORMATION: FR2 region of nanobody 2C5

<400> SEQUENCE: 12

Leu Ala Trp Phe Arg Gln Ala Pro Gly Lys Glu Arg Glu Phe Val Ala
 1               5                  10                  15

Ser

<210> SEQ ID NO 13
<211> LENGTH: 38
<212> TYPE: PRT
<213> ORGANISM: Artificial Sequence
<220> FEATURE:
<223> OTHER INFORMATION: FR3 region of nanobody 2C5

<400> SEQUENCE: 13

Tyr Tyr Glu Asp Ser Val Lys Gly Arg Phe Thr Ile Ser Arg Asp Asn
 1               5                  10                  15

Ser Lys Asn Thr Val Leu Leu Gln Met Asn Ser Leu Thr Pro Glu Asp
             20                  25                  30

Thr Ala Val Tyr Tyr Cys
         35

<210> SEQ ID NO 14
<211> LENGTH: 11
<212> TYPE: PRT
<213> ORGANISM: Artificial Sequence
<220> FEATURE:
<223> OTHER INFORMATION: FR4 region of nanobody 2C5

<400> SEQUENCE: 14

Trp Gly Gln Gly Thr Gln Val Thr Val Ser Ser

<210> SEQ ID NO 15
<211> LENGTH: 25
<212> TYPE: PRT
<213> ORGANISM: Artificial Sequence
<220> FEATURE:
<223> OTHER INFORMATION: FR1 region of nanobody S2T2M2_E6

<400> SEQUENCE: 15

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 16
<211> LENGTH: 17
<212> TYPE: PRT
<213> ORGANISM: Artificial Sequence
<220> FEATURE:
<223> OTHER INFORMATION: FR2 region of nanobody S2T2M2_E6

<400> SEQUENCE: 16

Met Gly Trp Phe Arg Gln Ala Pro Gly Lys Glu Arg Glu Phe Val Ala
1               5                   10                  15

Ser

<210> SEQ ID NO 17
<211> LENGTH: 38
<212> TYPE: PRT
<213> ORGANISM: Artificial Sequence
<220> FEATURE:
<223> OTHER INFORMATION: FR3 region of nanobody S2T2M2_E6

<400> SEQUENCE: 17

Arg Tyr Ala Asp Ala Val Lys Gly Arg Phe Thr Ile Ser Arg Asp Asn
1               5                   10                  15

Thr Asn Asn Thr Val Tyr Leu Leu Met Asn Asn Leu Lys Pro Glu Asp
            20                  25                  30

Thr Ala Val Tyr Tyr Cys
        35

<210> SEQ ID NO 18
<211> LENGTH: 11
<212> TYPE: PRT
<213> ORGANISM: Artificial Sequence
<220> FEATURE:
<223> OTHER INFORMATION: FR4 region of nanobody S2T2M2_E6

<400> SEQUENCE: 18

Trp Gly Gln Gly Thr Gln Val Thr Val Ser Ser
1               5                   10

<210> SEQ ID NO 19
<211> LENGTH: 143
<212> TYPE: PRT
<213> ORGANISM: Artificial Sequence
<220> FEATURE:
<223> OTHER INFORMATION: variable region of nanobody 2C5 with tag Myc
      and His

<400> SEQUENCE: 19

Gln Val Gln Leu Val Gln Ser Gly Gly Gly Leu Val Gln Ala Gly Gly
1               5                   10                  15

Ser Leu Arg Leu Ser Cys Ala Ala Ser Gly Arg Thr Phe Ser Ser Asp
            20                  25                  30

Thr Leu Ala Trp Phe Arg Gln Ala Pro Gly Lys Glu Arg Glu Phe Val
        35                  40                  45

Ala Ser Ile Ser Pro Ser Gly Gly Val Thr Tyr Tyr Glu Asp Ser Val
    50                  55                  60

Lys Gly Arg Phe Thr Ile Ser Arg Asp Asn Ser Lys Asn Thr Val Leu
65                  70                  75                  80

Leu Gln Met Asn Ser Leu Thr Pro Glu Asp Thr Ala Val Tyr Tyr Cys
                85                  90                  95

Asn Arg Asp Pro Lys Tyr Gly Asn Thr Arg Tyr Trp Gly Gln Gly Thr
            100                 105                 110

Gln Val Thr Val Ser Ser Ala Ala Ala Glu Gln Lys Leu Ile Ser Glu
        115                 120                 125

Glu Asp Leu Asn Gly Ala Ala His His His His His His Gly Ser
            130                 135                 140

<210> SEQ ID NO 20
<211> LENGTH: 146
<212> TYPE: PRT
<213> ORGANISM: Artificial Sequence
<220> FEATURE:
<223> OTHER INFORMATION: variable region of nanobody S2T2M3_E6 with tag
      Myc and His

<400> SEQUENCE: 20

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Arg Tyr
            20                  25                  30

Ala Met Gly Trp Phe Arg Gln Ala Pro Gly Lys Glu Arg Glu Phe Val
        35                  40                  45

Ala Ser Ile Ser Arg Ser Gly Gly Ser Thr Arg Tyr Ala Asp Ala Val
    50                  55                  60

Lys Gly Arg Phe Thr Ile Ser Arg Asp Asn Thr Asn Asn Thr Val Tyr
65                  70                  75                  80

Leu Leu Met Asn Asn Leu Lys Pro Glu Asp Thr Ala Val Tyr Tyr Cys
                85                  90                  95

Thr Ala Arg Arg Ile Ser Gly Thr Pro Gln Trp His Tyr Trp Gly
            100                 105                 110

Gln Gly Thr Gln Val Thr Val Ser Ser Ala Ala Ala Glu Gln Lys Leu
        115                 120                 125

Ile Ser Glu Glu Asp Leu Asn Gly Ala Ala His His His His His His
    130                 135                 140

Gly Ser
145

<210> SEQ ID NO 21
<211> LENGTH: 441
<212> TYPE: PRT
<213> ORGANISM: Homo sapiens

<400> SEQUENCE: 21

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

-continued

```
Gln Asp Gln Glu Gly Asp Thr Asp Ala Gly Leu Lys Glu Ser Pro Leu
         35                  40                  45

Gln Thr Pro Thr Glu Asp Gly Ser Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
                115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
                195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
                275                 280                 285

Ser Lys Cys Gly Ser Lys Asp Asn Ile Lys His Val Pro Gly Gly Gly
        290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
                355                 360                 365

Lys Lys Ile Glu Thr His Lys Leu Thr Phe Arg Glu Asn Ala Lys Ala
        370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
        435                 440
```

-continued

```
<210> SEQ ID NO 22
<211> LENGTH: 412
<212> TYPE: PRT
<213> ORGANISM: Homo sapiens

<400> SEQUENCE: 22
```

| | | | | | | | | | | | | | | | |
|---|---|---|---|---|---|---|---|---|---|---|---|---|---|---|---|
| Met | Ala | Glu | Pro | Arg | Gln | Glu | Phe | Glu | Val | Met | Glu | Asp | His | Ala | Gly |
| 1 | | | | 5 | | | | | 10 | | | | | 15 | |
| Thr | Tyr | Gly | Leu | Gly | Asp | Arg | Lys | Asp | Gln | Gly | Gly | Tyr | Thr | Met | His |
| | | | 20 | | | | | 25 | | | | | 30 | | |
| Gln | Asp | Gln | Glu | Gly | Asp | Thr | Asp | Ala | Gly | Leu | Lys | Glu | Ser | Pro | Leu |
| | | 35 | | | | | 40 | | | | | 45 | | | |
| Gln | Thr | Pro | Thr | Glu | Asp | Gly | Ser | Glu | Glu | Pro | Gly | Ser | Glu | Thr | Ser |
| | 50 | | | | | 55 | | | | | 60 | | | | |
| Asp | Ala | Lys | Ser | Thr | Pro | Thr | Ala | Glu | Ala | Glu | Glu | Ala | Gly | Ile | Gly |
| 65 | | | | | 70 | | | | | 75 | | | | | 80 |
| Asp | Thr | Pro | Ser | Leu | Glu | Asp | Glu | Ala | Ala | Gly | His | Val | Thr | Gln | Ala |
| | | | | 85 | | | | | 90 | | | | | 95 | |
| Arg | Met | Val | Ser | Lys | Ser | Lys | Asp | Gly | Thr | Gly | Ser | Asp | Asp | Lys | Lys |
| | | | 100 | | | | | 105 | | | | | 110 | | |
| Ala | Lys | Gly | Ala | Asp | Gly | Lys | Thr | Lys | Ile | Ala | Thr | Pro | Arg | Gly | Ala |
| | | 115 | | | | | 120 | | | | | 125 | | | |
| Ala | Pro | Pro | Gly | Gln | Lys | Gly | Gln | Ala | Asn | Ala | Thr | Arg | Ile | Pro | Ala |
| | 130 | | | | | 135 | | | | | 140 | | | | |
| Lys | Thr | Pro | Pro | Ala | Pro | Lys | Thr | Pro | Ser | Ser | Gly | Glu | Pro | Pro | |
| 145 | | | | | 150 | | | | | 155 | | | | | 160 |
| Lys | Ser | Gly | Asp | Arg | Ser | Gly | Tyr | Ser | Ser | Pro | Gly | Ser | Pro | Gly | Thr |
| | | | | 165 | | | | | 170 | | | | | 175 | |
| Pro | Gly | Ser | Arg | Ser | Arg | Thr | Pro | Ser | Leu | Pro | Thr | Pro | Pro | Thr | Arg |
| | | | 180 | | | | | 185 | | | | | 190 | | |
| Glu | Pro | Lys | Lys | Val | Ala | Val | Val | Arg | Thr | Pro | Pro | Lys | Ser | Pro | Ser |
| | | 195 | | | | | 200 | | | | | 205 | | | |
| Ser | Ala | Lys | Ser | Arg | Leu | Gln | Thr | Ala | Pro | Val | Pro | Met | Pro | Asp | Leu |
| | 210 | | | | | 215 | | | | | 220 | | | | |
| Lys | Asn | Val | Lys | Ser | Lys | Ile | Gly | Ser | Thr | Glu | Asn | Leu | Lys | His | Gln |
| 225 | | | | | 230 | | | | | 235 | | | | | 240 |
| Pro | Gly | Gly | Gly | Lys | Val | Gln | Ile | Ile | Asn | Lys | Lys | Leu | Asp | Leu | Ser |
| | | | | 245 | | | | | 250 | | | | | 255 | |
| Asn | Val | Gln | Ser | Lys | Cys | Gly | Ser | Lys | Asp | Asn | Ile | Lys | His | Val | Pro |
| | | | 260 | | | | | 265 | | | | | 270 | | |
| Gly | Gly | Gly | Ser | Val | Gln | Ile | Val | Tyr | Lys | Pro | Val | Asp | Leu | Ser | Lys |
| | | 275 | | | | | 280 | | | | | 285 | | | |
| Val | Thr | Ser | Lys | Cys | Gly | Ser | Leu | Gly | Asn | Ile | His | His | Lys | Pro | Gly |
| | 290 | | | | | 295 | | | | | 300 | | | | |
| Gly | Gly | Gln | Val | Glu | Val | Lys | Ser | Glu | Lys | Leu | Asp | Phe | Lys | Asp | Arg |
| 305 | | | | | 310 | | | | | 315 | | | | | 320 |
| Val | Gln | Ser | Lys | Ile | Gly | Ser | Leu | Asp | Asn | Ile | Thr | His | Val | Pro | Gly |
| | | | | 325 | | | | | 330 | | | | | 335 | |
| Gly | Gly | Asn | Lys | Lys | Ile | Glu | Thr | His | Lys | Leu | Thr | Phe | Arg | Glu | Asn |
| | | | 340 | | | | | 345 | | | | | 350 | | |
| Ala | Lys | Ala | Lys | Thr | Asp | His | Gly | Ala | Glu | Ile | Val | Tyr | Lys | Ser | Pro |
| | | 355 | | | | | 360 | | | | | 365 | | | |
| Val | Val | Ser | Gly | Asp | Thr | Ser | Pro | Arg | His | Leu | Ser | Asn | Val | Ser | Ser |
| | 370 | | | | | 375 | | | | | 380 | | | | |

```
Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
            405                 410
```

<210> SEQ ID NO 23
<211> LENGTH: 383
<212> TYPE: PRT
<213> ORGANISM: Homo sapiens

<400> SEQUENCE: 23

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350
```

Val Ser Ser Thr Gly Ser Ile Asp Met Val Asp Ser Pro Gln Leu Ala
    355                 360                 365

Thr Leu Ala Asp Glu Val Ser Ala Ser Leu Ala Lys Gln Gly Leu
    370                 375                 380

<210> SEQ ID NO 24
<211> LENGTH: 410
<212> TYPE: PRT
<213> ORGANISM: Homo sapiens

<400> SEQUENCE: 24

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
        275                 280                 285

Ser Lys Cys Gly Ser Leu Gly Asn Ile His His Lys Pro Gly Gly Gly
    290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
                325                 330                 335

Asn Lys Lys Ile Glu Thr His Lys Leu Thr Phe Arg Glu Asn Ala Lys

```
              340                 345                 350
Ala Lys Thr Asp His Gly Ala Glu Ile Val Tyr Lys Ser Pro Val Val
            355                 360                 365

Ser Gly Asp Thr Ser Pro Arg His Leu Ser Asn Val Ser Ser Thr Gly
370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 25
<211> LENGTH: 381
<212> TYPE: PRT
<213> ORGANISM: Homo sapiens

<400> SEQUENCE: 25

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Pro Gly Ser Glu Thr Ser
        50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
            260                 265                 270

Gly Gly Gly Gln Val Glu Val Lys Ser Glu Lys Leu Asp Phe Lys Asp
        275                 280                 285

Arg Val Gln Ser Lys Ile Gly Ser Leu Asp Asn Ile Thr His Val Pro
290                 295                 300
```

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
            325                 330                 335

Pro Val Val Ser Gly Asp Thr Ser Pro Arg His Leu Ser Asn Val Ser
            340                 345                 350

Ser Thr Gly Ser Ile Asp Met Val Asp Ser Pro Gln Leu Ala Thr Leu
            355                 360                 365

Ala Asp Glu Val Ser Ala Ser Leu Ala Lys Gln Gly Leu
370                 375                 380

<210> SEQ ID NO 26
<211> LENGTH: 352
<212> TYPE: PRT
<213> ORGANISM: Homo sapiens

<400> SEQUENCE: 26

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
    290                 295                 300

```
Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
                340                 345                 350

<210> SEQ ID NO 27
<211> LENGTH: 18
<212> TYPE: PRT
<213> ORGANISM: Artificial Sequence
<220> FEATURE:
<223> OTHER INFORMATION: truncated protein Tau consisting of the 3R
      region

<400> SEQUENCE: 27

Val Gln Ile Val Tyr Lys Pro Val Asp Leu Ser Lys Val Thr Ser Lys
1               5                   10                  15

Cys Gly
```

ANTI-TAU NANOBODIES

The present invention relates to anti-Tau nanobodies.

The is currently a consensus which considers the sporadic form of Alzheimer's disease (AD) to be a continuum, from a preclinical asymptomatic form to a disease clinically characterized by means of cognitive and memory tests, and also by means of various biomarkers (Dubois et al. *Lancet Neurology*, 13, 614-629 (2014)). However, the development of new therapeutic strategies demands diagnostic methods that allow early detection and make it possible to monitor the neurodegenerative signs in the population at risk in order to choose the patients who should be treated and to control the effects of the treatments.

AD is defined by the combination of a syndrome of progressive dementia and of two characteristic brain lesions: extracellular senile plaques (APs), composed of amyloid peptide (Aβ) and neurofibrillary degenerations (NFDs) composed of hyper-phosphorylated Tau protein aggregates. The NFDs appear in the entorhinal cortical structures before the APs are observed in the cortex (Braak et al. *Journal of Neuropathological Experimental Neurology*, 70 (11): 960-969 (2011)). Furthermore, the cortical distribution and the number of NFDs correlate with memory problems in patients suffering from AD (Nelson et al. *Journal of Neuropathological Experimental Neurology*, 71 (5); 362-381 (2012)). Recently, it has been shown that the oligomeric forms of Tau represent the toxic forms (Usenovic et al. *Journal of Neuroscience*, 35 (42): 14234-14250 (2015)) involved in the propagation (Goedert et al. *Current Neurology and Neuroscience*, 14: 495 (2014)) of tauopathies, such as AD, by gradual contamination of the neurons.

Nuclear brain imaging (single-photon emission computed tomography (SPECT) and positron emission tomography (PET)) is an appropriate tool for determining the presence and the progression of the molecular lesions associated with AD (Dubois et al. *Alzheimer's & Dementia*, 12 (3): 292-323 (2016)). Radioligands of APs are already available (Catafau and Bullich, *Clinical and Translational Imaging*, 3 (1): 39-55 (2015)) as are some radio tracers. Tracers which target the β-sheets within NFDs are currently in the process of being developed. Two of them, 18F-AV-1451 (Ossenkoppele et al. *Brain*, 139 (5): 1551-1567 (2016)) and 18F-THK5117 (Jonasson et al. *Journal of Nuclear Medicine*, 57 (4): 574-581 (2016)), might facilitate the stratification of patients suffering from NFD-type lesions. On the other hand, none of them make it possible to detect and monitor the soluble oligomeric forms of Tau.

Under physiological conditions, the highly soluble Tau protein interacts with the microtubules to stabilize them, its partial phosphorylation allowing its alternating detachment from the microtubules. The Tau protein is normally very soluble and is in non-structured form. Under certain pathological conditions, post-translational modifications of Tau, in particular hyperphosphorylation, cause the protein to become structured and to form aggregates: dimers, oligomers, fibers: helicoidal pairs of filaments resulting in the formation of NFDs. Predominant importance is currently assigned to Tau oligomers, from the point of view of both the toxicity and the propagation of the lesions of AD and of other tauopathies.

scFvs directed against the Tau protein in the form of oligomers, in particular in the form of dimers and trimers, have been described in application US 2015/0266947. These scFvs, approximately 30 kDa in size, are not directed against Tau in fiber form.

With the aim of developing new markers for the pathological forms of Tau for nuclear imaging targeting the various aggregated forms of this molecule, the present inventors have developed nanobodies (Nbs), in particular VHHs, by targeting the pathological forms, in particular the early pathological forms, of Tau, more particularly Tau in oligomer form and optionally in fiber form. These nanobodies are thus capable of improving the diagnosis and the monitoring of AD, and also the evaluation of the effects of potential treatments.

These nanobodies also make it possible to target and therefore identify the presence of the pathological forms of Tau in tauopathies other than AD. The nanobodies according to the invention, which are in VHH format, are small fragments of antibodies corresponding to the variable domains of the heavy chains of certain camelid antibodies. They are the smallest functional elements (10-15 kDa) derived from immunoglobulins having an antigen-binding domain and they exhibit affinities toward the antigen of about one nanomolar. Because of their simple structure without an Fc-type domain and their low molecular weight, they are appropriate tools for crossing the blood-brain barrier (Caljon et al. *British Journal of Pharmacology*, 165 (7): 2341-2353 (2012)).

SUMMARY OF THE INVENTION

The present invention thus relates to a nanobody which binds to the pathological forms of the Tau protein, in particular the early pathological forms of Tau, such as Tau in oligomer form and optionally Tau in fiber form.

A subject of the present invention is thus a nanobody directed against the Tau protein in oligomer form and directed against the Tau protein in fiber form.

The present invention also relates to a nanobody directed against the Tau protein, said Tau protein being in oligomer form and said nanobody being devoid of light chain.

A subject of the present invention is thus a nanobody directed against the Tau protein, said Tau protein being in pathological form, in particular in oligomer form, and said nanobody competing for binding to the Tau protein in oligomer form with a nanobody comprising the amino acid sequences:
(i) GRTFSX$_1$X$_2$X$_3$ (SEQ ID No. 1) as CRD1 in which the amino acid X$_1$ is S or R, X$_2$ is D or Y and X$_3$ is T or A,
(ii) ISX$_1$SGGX$_2$T (SEQ ID No. 2) as CRD2 in which the amino acid X$_1$ is P or R and X$_2$ is S or V, and
(iii) NRDPKYGNTRY (SEQ ID No. 5) or TARRRISGT-PQWHY (SEQ ID No. 8) as CRD3.

The present invention further relates to a nanobody directed against the Tau protein, said Tau protein being in pathological form, in particular in oligomer form, and said nanobody competing for binding to the Tau protein in oligomer form with a nanobody comprising:
 a) the amino acid sequences (i) GRTFSSDT (SEQ ID No. 3) as CRD1, (ii) ISPSGGVT (SEQ ID No. 4) as CRD2 and (iii) NRDPKYGNTRY (SEQ ID No. 5) as CRD3; or
 b) the amino acid sequences (i) GRTFSRYA (SEQ ID No. 6) as CRD1, (ii) ISRSGGST (SEQ ID No. 7) as CRD2 and (iii) TARRRISGTPQWHY (SEQ ID No. 8) as CRD3.

The present invention also relates to nanobodies directed against the Tau protein, said nanobodies comprising the amino acid sequences:
(i) GRTFSX$_1$X$_2$X$_3$ (SEQ ID No. 1) as CRD1 in which the amino acid X$_1$ is S or R, X$_2$ is D or Y and X$_3$ is T or A, (ii) ISX$_1$SGGX$_2$T (SEQ ID No. 2) as CRD2 in which the amino acid X$_1$ is P or R and X$_2$ is S or V, and (iii) NRDPKYGNTRY (SEQ ID No. 5) or TARRRISGT-PQWHY (SEQ ID No. 8) as CRD3.

The invention further relates to nanobodies, directed against the Tau protein, comprising:
a) the amino acid sequences (i) GRTFSSDT (SEQ ID No. 3) as CRD1, (ii) ISPSGGVT (SEQ ID No. 4) as CRD2 and (iii) NRDPKYGNTRY (SEQ ID No. 5) as CRD3; or
b) the amino acid sequences (i) GRTFSRYA (SEQ ID No. 6) as CRD1, (ii) ISRSGGST (SEQ ID No. 7) as CRD2 and (iii) TARRRISGTPQWHY (SEQ ID No. 8) as CRD3; or
a functionally conservative variant of the nanobody defined in a) or b) comprising a conservative substitution of one or two amino acids in, respectively, one, two or three of the sequences SEQ ID No. 3, SEQ ID No. 4 and SEQ ID No. 5, or SEQ ID No. 6, SEQ ID No. 7 and SEQ ID No. 8.

The present invention also relates to the nanobodies as defined above, for use thereof as a contrast agent in noninvasive, in vivo medical imaging, for use thereof in diagnostic or prognostic methods, preferably for the diagnosis or prognosis of a tauopathy, or for use thereof as a medicament.

A subject of the invention is also the use of this nanobody for the in vitro detection of the Tau protein, in particular in pathological form, preferably in an early pathological form, more particularly in oligomer form and optionally in fiber form, in a sample.

Finally, the invention relates to a pharmaceutical composition comprising this nanobody in combination with a pharmaceutically acceptable carrier.

DETAILED DESCRIPTION OF THE INVENTION

Tauopathy

The term "tauopathy" groups together about twenty pathological conditions which have in common the existence of intracerebral deposits of Tau protein, in particular in pathological form, and which share clinical, pathological, biochemical and genetic similarities. The term "intracerebral deposits of Tau protein" means the presence of Tau aggregates and thus the presence of Tau in pathological form.

Certain tauopathies, such as progressive supranuclear paralysis, corticobasal degeneration and Gerstmann-Straussler-Scheinker disease, are characterized by the presence of neurofibrillary degenerations (NFDs) which cannot be distinguished from those of Alzheimer's disease. In this case, the term "intracerebral deposits of Tau protein" or "presence of the pathological forms of Tau" denotes for example the presence of neurofibrillary degenerations (NFDs).

Pick's disease for example is characterized by spherical neuronal inclusions called Pick's bodies. These Pick's bodies consist of disorganized straight filaments and thus also of a pathological form of Tau.

"Neurofibrillary degeneration" (also known as neurofibrillary tangles) denotes zones, for example in the cerebral cortex, inside which the neuronal population exhibits, around the nucleus and in the cell extensions, fibrillary tangles consisting of paired helical filaments (PHFs) and/or of straight filaments (SFs).

It should be noted that NFD formation comprises the aggregation of Tau, also known as "fibrillar aggregation" or "fibrillogenesis". During this process, the Tau protein becomes organized in the form of oligomers and then in the form of fibers which become organized in the form of helical pairs of filaments and in the form of straight filaments. The paired helical filament forms and the straight filament forms constitute the NFDs.

The term "pathological form of Tau" encompasses the Tau protein in oligomer form, in fiber form, in paired helical filament form and in straight filament form. However, it has been discovered that the intermediate aggregation forms, that is to say Tau in oligomer forms, and Tau in fiber form, are toxic, the oligomers being the most toxic. They are targeted by the term "early pathological forms of Tau" which thus means in particular Tau in oligomer form and in fiber forms, more particularly Tau in oligomer form.

The Tau protein is an intracellular protein; however, the pathological forms of Tau may, in certain cases, be extracellular.

In one particular embodiment, the pathological forms of Tau, preferably Tau in oligomer form, are extracellular.

Consequently, in one embodiment, "a pathological form of Tau" refers to Tau in oligomer form, in fiber forms, in paired helical filament form and/or in straight filament forms. Preferably, a pathological form of Tau is an early pathological form of Tau, more particularly Tau in oligomer form and optionally Tau in fiber form, for example Tau in oligomer form or Tau in fiber form.

In one embodiment, "tauopathy" means a disease which is associated with the existence of the pathological forms of Tau, as defined above. The tauopathy is chosen from Alzheimer's disease, progressive supranuclear paralysis (or Steele-Richardson-Olzewski disease) corticobasal degeneration, Pick's disease, Niemann-Pick disease type C, Gerstmann-Straussler-Scheinker disease and frontotemporal degeneration linked to a chromosome 17 mutation, preferably Alzheimer's disease, progressive supranuclear paralysis, corticobasal degeneration and Gerstmann-Straussler-Scheinker disease, in particular Alzheimer's disease.

Tau

The term "Tau protein" or "Tau" denotes the Tau (tubule-associated unit) protein which is a mammalian protein. The Tau protein is a member of the family of microtubule associating proteins (MAPs). It is encoded by the MAPT gene located on chromosome 17, at position 17q21. The Tau protein is also known as MSTD; PPND, DDPAC; MAPTL; MTBT1; MTBT2; FTDP-17; PPP1R103. In human beings, the Tau protein is synthesized essentially in the neurons.

The primary transcript of Tau contains 16 exons. In the brain, some exons are not translated. Exons 2, 3 and 10 are alternatively spliced and are specific to adult brain tissue. The alternative splicing of these 3 exons produces 6 possible combinations (2−3−10− to 2+3+10+). At the protein level, there are thus six isoforms of Tau proteins in the adult brain. It should be noted that Tau protein expression is regulated during development. Thus, a single isoform, termed fetal isoform, is present at birth and does not comprise inserts encoded by exons 2, 3 or 10. The other isoforms appear during subsequent development. The length of their sequences ranges from 352 to 441 amino acids.

The amino-terminal portion of Tau proteins, also known as projection domain, has a role that is still poorly understood. This projection domain might interact with the plasma membrane and certain organelles such as the mitochondria. As for the carboxy-terminal domain, it comprises 3 (without exon 10) or 4 (with exon 10) repeat segments, specific binding domains (called 3R or 4R) comprising the conserved motif of the tubulin-binding domain, which controls the microtubule stability. These R motifs constitute the anchoring point of the Tau protein on the microtubules. The three isoforms without the sequence encoded by exon 10 (10−) have three microtubule-binding domains (3R), also called 2N3R, 1N3R and 0N3R, and differ by virtue of the amino-terminal portion. The three isoforms with the sequence encoded by exon 10 have four microtubule-binding domains (4R), are called 2N4R, 1N4R and 0N4R, and also differ by virtue of the amino-terminal portion. The interaction with tubulin dimers is greater with this fourth domain, which further stabilizes the microtubules and can modulate neurite extension length, and also neuronal plasticity.

In one embodiment of the invention, said Tau protein is selected from the group consisting of the 2N4R, 1N4R, 0N4R, 2N3R, 1N3R and 0N3R isoforms. The Tau protein is preferably in the 2N4R isoform.

The amino acid sequence of the 2N4R isoform of the Tau protein, also called Tau-F or Tau441 or htau40, with 441 amino acids, can be found on the UniprotKb database in its version of Nov. 16, 2016, under accession number P10636-8 (SEQ ID No. 21).

The amino acid sequence of the 1N4R isoform of the Tau protein, also called Tau-E or Tau412, with 412 amino acids, can be found on the UniprotKb database in its version of Nov. 16, 2016, under accession number P10636-7 (SEQ ID No. 22).

The amino acid sequence of the 0N4R isoform of the Tau protein, also called Tau-D or Tau383, with 383 amino acids, can be found on the UniprotKb database in its version of Nov. 16, 2016, under accession number P10636-6 (SEQ ID No. 23).

The amino acid sequence of the 2N3R isoform of the Tau protein, also called Tau-C or Tau410, with 410 amino acids, can be found on the UniprotKb database in its version of Nov. 16, 2016, under accession number P10636-5 (SEQ ID No. 24).

The amino acid sequence of the 1N3R isoform of the Tau protein, also called Tau-B or Tau 381, with 381 amino acids, can be found on the UniprotKb database in its version of Nov. 16, 2016, under accession number P10636-5 (SEQ ID No. 25).

The amino acid sequence of the 0N3R isoform of the Tau protein, also called Fetal-Tau or Tau 352, with 352 amino acids, can be found on the UniprotKb database in its version of Nov. 16, 2016, under accession number P10636-2 (SEQ ID No. 26).

The Tau protein is a neuronal protein which is often located in the axon, more rarely in the dendrites and exceptionally in the cell body. In native form, Tau is a non-structured protein in the form of a monomer. Consequently, in the context of the present invention, the term "native Tau" means the Tau protein in monomeric form and vice versa. The function of the Tau proteins in native form is to interact with the microtubules via specific binding domains (3R and 4R) and to promote microtubule assembly and stability. The interaction of the Tau protein with the microtubules is mainly regulated by phosphorylation. Tau is a phosphoprotein which contains approximately 80 potential phosphorylation sites. The regulation of the Tau protein phosphorylation state is a result of the combined activities of protein kinases and of protein phosphatases.

In general, hyperphosphorylation of the Tau protein, in particular in the specific binding domains (3R and 4R), decreases its affinity for microtubules, which can lead to destabilization of the latter and, consequently, to a disorganization of the cytoskeleton. In addition, this hyperphosphorylation can lead to the aggregation of Tau and thus the formation of NFDs, as described above in the "tauopathy" section.

Those skilled in the art distinguish abnormal phosphorylation and hyperphosphorylation of the Tau protein.

"Abnormal phosphorylation" consists of phosphorylation in sites which, under physiological conditions, are not subject to phosphorylation. Reference is made to a non-physiological epitope; these are, for example, epitopes recognized by the AT100 and TG-3 antibodies.

On the other hand, the term "hyperphosphorylated" means phosphorylation at the level of physiological epitopes in greater number than in a normal adult brain or when, for a given site, a high percentage of Tau protein is phosphorylated.

Hyperphosphorylation of the Tau protein can lead to the detachment of tau from the microtubules and an increase in the intracellular concentration of tau, causing the formation of oligomers and then fibers, until there is formation of paired helical filaments and straight filaments, the tangling of which will constitute fibrillary degenerations. The result is an accumulation of tau protein in the neurons and involves more than 20 different neurodegenerative diseases called tauopathy. The accumulation of the Tau protein is even sometimes the only cause of such a tauopathy.

It is known to those skilled in the art that Tau aggregation can be studied by using the non-phosphorylated Tau protein (Xu, S et al. Alzheimer's Dement. 2010 Mar. 6 (2): 110-7, Kumar S. et al. J Biol Chem. 2014 Jul. 18; 289 (29): 20318-32; Flach, K et al. J Biol Chem. 2012 Dec. 21; 287 (52): 43223-33).

The inventors of the present invention have developed the nanobodies of the invention directed against the non-phosphorylated Tau protein, in particular in oligomer form. However, as demonstrated by immunohistochemistry, the nanobodies of the invention also bind specifically to the Tau protein in neurofibrillary degenerations in sections of human brains in which the Tau protein is present in phosphorylated form.

Consequently, in one embodiment of the invention, the Tau protein is non-phosphorylated and/or phosphorylated.

In certain intracerebral deposits of Tau protein, said protein may also be degraded and lose the N-terminal portion while retaining the microtubule-binding domains. This truncated Tau protein comprises the carboxy-terminal portion of the Tau proteins and thus, depending on the starting isoform, either the 3R region (R1, R2, R3, R4) or the 4R region (R1, R3 and R4). This proteolysis promotes the formation of fibers and then the aggregation of the paired helical filaments which become insoluble and are also indicators of certain tauopathies.

Consequently, in one embodiment, the Tau protein is a truncated Tau protein comprising the carboxy-terminal portion of the Tau protein, in particular the R3 or R4 region of the repeat motifs of Tau, preferably the R3 region. Preferably, the truncated Tau protein is devoid of the N-terminal domains. In one particular embodiment, the Tau protein comprises or consists of a peptide having the amino acid sequence VQIVYKPVDLSKVTSKCG (SEQ ID No. 27) which corresponds to amino acids 306 to 323 of tau441, as defined above.

Anti-Tau Nanobodies

In the context of the present invention, the terms "antibody" and "immunoglobulin" have the same meaning and are used without distinction. In conventional antibodies, the two heavy chains are linked to one another by disulfide bridges and each heavy chain is linked to a light chain by a disulfide bridge. There are two types of light chain: lambda (λ) and kappa (κ) light chains. There are five main classes of heavy chains (or isotopes) which determine the functional activity of an antibody: IgM, IgD, IgG, IgA and IgE. Each chain contains domains of distinct sequence. The light chain comprises two domains: a variable domain (VL) and a constant domain (CL). The heavy chain comprises four domains: a variable domain (VH) and three constant domains (CH1, CH2 and CH3, collectively referred to as CH). The variable regions of the heavy (VH) and light (VL) chains determine the binding recognition and the antigen specificity. The domains of the constant regions of the light (CL) and heavy (CH) chains confer important biological properties such as antibody chain association, secretion, transplacental mobility, complement binding and Fc receptor binding. The Fv fragment is the N-terminal portion of the Fab fragment of an immunoglobulin consisting of the variable portions of a light chain and of a heavy chain. The specificity of the antibody lies in the structural complementarity between the antibody combining site and the antigenic determinant. The antibody combining sites are made of residues which come mainly from the hypervariable regions or complementarity-determining regions (CDRs). Occasionally, residues originating from the non-hypervariable regions or "framework" (FR) regions can influence the overall structure of the domain and consequently the combining site.

In the context of the invention, the term "CDR" refers to the amino acid sequences which, together, define the binding affinity and the specificity of the natural Fv region of a native binding site of an immunoglobulin. The heavy and light chains of an immunoglobulin each have three CDRs, denoted H-CDR1, H-CDR2, H-CDR3 and L-CDR1, L-CDR2, L-CDR3 respectively. An antigen-binding site thus includes 6 CDRs, comprising all of the CDRs of a variable region of a heavy chain and of a variable region of a light chain.

The location of the CDRs in the sequence of an antibody or of a nanobody can be determined by those skilled in the art using techniques previously described. Typically, the CDRs can be identified by sequencing the DNA of the antibody or of the nanobody with an appropriate system, such as the 3730XL DNA Analyzer and ABI PRISM BigDye Terminator cyc, then by analyzing the sequences thus obtained using dedicated databases such as the International ImMunoGeneTics Database or IMGT (Lefranc (2003) Dev. Comp. Immunol. 27: 55) or Kabat, et al. (Sequences of Proteins of Immunological Interest (National Institutes of Health, Bethesda, Md., 1991)), preferably IMGT.

In the context of the invention the term "framework region", "framework" or "FR" refer to the amino acid sequences inserted between the CDRs.

In the context of the invention, the terms "nanobody", "VHH", "VHH antibody fragment" and "single-domain antibody" are used without distinction and denote the variable domain of the single heavy chain of antibodies of the type of those found in camelids, which are naturally devoid of light chains. In the absence of a light chain, the nanobodies each have three CDRs, denoted CDR1, CDR2 and CDR3 respectively. The nanobodies according to the invention can in particular be camel, dromedary, llama or alpaca nanobodies. Preferably, the nanobodies according to the invention are llama nanobodies.

The expression "nanobody directed against the Tau protein" is intended to mean herein a nanobody capable of selectively binding to the Tau protein, as defined in the "Tau" section. Preferentially, the nanobody is Tau-specific, that is to say that it binds to Tau to the exclusion of any other molecule.

The inventors have prepared nanobodies directed against pathological forms of the Tau protein, such as the Tau protein in oligomer form and optionally in fiber form. The nanobodies can also be directed against the truncated Tau protein in fiber form.

In particular, the inventors have immunized llamas with a preparation of Tau proteins enriched with Tau protein in oligomer form, with a preparation of Tau proteins enriched with Tau protein in fiber form and a preparation of truncated Tau proteins enriched with truncated Tau protein in fiber form. The inventors have subsequently identified more precisely two nanobodies directed against Tau and having unexpected additional characteristics which other anti-Tau nanobodies do not have. Specifically, these two nanobodies, 2C5 and S2T2M3_E6, in particular 2C5, recognize Tau in oligomer form and optionally in fiber form. The Tau protein in fiber form is also recognized when it is a truncated Tau protein as defined above. At the same time, these two nanobodies, 2C5 and S2T2M3_E6, in particular 2C5, do not bind to the native Tau protein, in monomer form. In addition, these two nanobodies, 2C5 and S2T2M3_E6, in particular 2C5, do not bind to amyloid beta peptide fibers.

Consequently, in one preferred embodiment, the nanobodies are directed against the Tau protein in oligomer form.

In the context of the present invention, the term "oligomers" relates to a preparation of Tau obtained by an in vitro fibrillation process as described in the examples of this application. Typically, the Tau fibrillation (40 μM) is carried out for example at 37° C. in buffer, for example MOPS (3-(N-morpholino)propanesulfonic acid), typically 20 mM, typically at pH 7, typically in the presence of heparin (10 μM) and of $NaN_3$ (4%) for a final volume of typically 1.5 ml. The fibrillation is typically stopped by freezing the samples at −80° C. after typically 48 hours so as to obtain Tau in oligomer form. Depending on the exact fibrillation time, this Tau protein preparation is enriched with Tau protein in oligomer form.

The term "enriched with Tau protein in oligomer form" means a preparation of Tau proteins in oligomer form, in which more than 50% of Tau proteins are in oligomer form. For example, more than 50%, more than 55%, more than 60%, more than 70%, more than 75%, more than 80%, more than 85%, more than 90% of the Tau proteins are in oligomer form. It is known to those skilled in the art that a preparation enriched with Tau proteins in oligomer form also contains Tau protein in native form and Tau protein in fiber form.

Consequently, in one embodiment, the Tau protein in oligomer form is a mixture of Tau proteins in monomer form, in oligomer form and in fiber form, in which more than 50% of the Tau proteins are in oligomer form, in particular more than 55%, more than 60%, more than 70%, more than 75%, more than 80%, more than 85%, more than 90% of the Tau proteins are in oligomer form.

It is also known to those skilled in the art that it is possible to purify the Tau protein in oligomer form from such a preparation, using several methods known to those skilled in the art, including for example size exclusion chromatography.

The oligomers preferably comprise between 2 and 45 Tau units. Oligomers having 2 to 8 Tau units are called soluble oligomers and oligomers having more than 8 up to 45 Tau units are called granular oligomers and may be soluble or insoluble. In one embodiment, these oligomers can be characterized, using atomic force microscopy or electron microscopy, as being round dots having a diameter of approximately 12 to 29 nm.

In another embodiment, these oligomers can be characterized using size exclusion chromatography as being spherical molecules having a diameter of approximately 12 to 35 nm.

Consequently, in the context of the invention, the term "oligomer" refers to a Tau aggregate or polymer having from 2 up to 50 Tau units, in particular 2 to 20, preferably 2 to 12 Tau units, for example a dimer, a trimer, a tetramer, a pentamer, a hexamer, heptamer, octamer, nonamer, decamer, undecamer or dodecamer of Tau or having 20 to 45, preferably 30 to 45 Tau units, for example 35 to 45, preferably 38 to 42 Tau units. In certain embodiments, the Tau protein is dimeric or trimeric. In certain embodiments, the Tau protein in oligomer form is soluble and/or insoluble, more preferably soluble.

In one embodiment, the nanobody of the invention has an affinity for the Tau protein in oligomer form which is 20 nM, for example ≤10 nM, ≤8 nM, ≤7 nM or ≤5 nM, for example an affinity of from 0.1 nM to 20 nM, in particular from 1 nM to 10 nM, or from 1 nM to 7 nM, for example 5 nM.

The term "affinity" is intended mean the binding capacity between a macromolecule and the antigen that it binds, in particular the binding capacity between a nanobody and the antigen that it binds, for example a nanobody of the invention and the Tau protein in the pathological forms as defined above.

The affinity and thus the capacity of the nanobody of the invention can bind to the Tau protein, for example in oligomer or fiber form, can be measured in vitro by several methods, including surface plasmon resonance (SPR, in particular using a BIAcore 2000 instrument—Pharmacia Biosensor, Uppsala, Sweden) or for example by means of an ELISA assay, as described in the examples.

In one embodiment, the nanobodies of the invention also bind to the Tau protein in fiber form.

In the context of the invention, the term "fibers" relates to a preparation of the Tau protein obtained by a fibrillation process as described in the examples of this application. Typically, the fibrillation of Tau (40 µM) is carried out for example at 37° C. in buffer, for example MOPS (3-(N-morpholino)propanesulfonic acid), typically 20 mM, typically at pH 7, typically in the presence of heparin (10 µM) and of NaN$_3$ (4%), for a final volume of typically 1.5 ml. The fibrillation is typically stopped by freezing the samples at −80° C. after typically 72 hours so as to obtain Tau in fiber form. Such a preparation of Tau proteins in fiber form is thus a preparation of Tau proteins enriched with Tau protein in fiber form.

The term "enriched with Tau in fiber form" means a preparation of Tau proteins in fiber form in which more than 50% of the Tau proteins are in fiber form. For example, more than 50%, more than 55%, more than 60%, more than 70%, more than 75%, more than 80%, more than 85%, more than 90% of the Tau proteins are in fiber form. It is known to those skilled in the art that a preparation enriched with Tau proteins in fiber form also contains the Tau protein in native form and Tau protein in oligomer form.

Consequently, in one embodiment, the Tau protein in fiber form is a mixture of Tau proteins in monomer form, in oligomer form and in fiber form, in which more than 50% of the Tau proteins are in fiber form, in particular more than 55%, more than 60%, more than 70%, more than 75%, more than 80%, more than 85%, more than 90% of the Tau proteins are in fiber form.

It is also known to those skilled in the art that it is possible to purify the Tau protein in fiber form from such a preparation, using several methods known to those skilled in the art, including for example size exclusion chromatography.

In the context of the invention, the term "fiber" describes an artificially obtained Tau polymer or aggregate which mimics in vivo Tau fibrillation and thus mimics the paired helical filaments and the straight filaments which make up NFDs. Consequently, the Tau fibers as used in the context of the invention encompass paired helical filaments and straight filaments. These fibers can be characterized, by electron microscopy, as having a filamentous appearance. In one embodiment, the nanobody of the invention has an affinity for the Tau protein in fiber form which is 20 nM, for example ≤10 nM, ≤8 nM, ≤7 nM or 6 nM, for example an affinity of from 0.1 nM to 20 nM, in particular from 1 nM to 10 nM, or from 1 nM to 8 nM, for example 6 nM.

In another embodiment, the nanobodies of the invention also bind to the truncated Tau protein. Preferably, this truncated protein is in fiber form and can also be referred to as R3 peptide fibers. The truncated Tau protein is as defined in the "Tau" section above. In particular, this truncated Tau protein comprises or consists of the amino acid sequence SEQ ID No. 27.

In one embodiment, the nanobody of the invention has an affinity for the truncated Tau protein in fiber form which is ≤100 nM, for example ≤80 nM, 70 nM, ≤60 nM or ≤50 nM, for example an affinity of from 1 nM to 100 nM, in particular from 1 nM to 80 nM, or from 40 nM to 60 nM, for example 50 nM.

In one embodiment, the nanobody of the invention has an affinity for the truncated Tau protein in fiber form which is 100 nM, for example an affinity of from 1 nM to 100 nM, in particular from 1 nM to 80 nM, from 1 nM to 20 nM, for example an affinity of from 10 to 20 nM.

In the context of the invention, "the truncated Tau protein in fiber form" or "the R3 peptide fibers" concerns a preparation of R3 peptide obtained by an in vitro fibrillation process as described in the examples of this application. Typically, the fibrillation of R3 (0.4 µM) is carried out for example at 37° C. in buffer, for example PBS (50 mM phosphate buffered saline), typically at pH 7, typically in the presence of heparin (0.4 µM) and of NaN$_3$ (4%), for a final volume of typically 1.5 ml. The fibrillation is typically stopped by freezing the samples at −80° C. after typically 72 hours so as to obtain truncated Tau (R3) in fiber form.

In one example, the affinity for the truncated Tau protein in fiber form is measured, for example, by ELISA, in, for example, a phosphate buffered saline buffer (NaCl, 137 mM; KCl, 2.7 mM; Na$_2$HOP$_4$, 10 mM; KH$_2$PO$_4$, 1.8 mM) comprising, for example, 1% BSA and having, for example, a pH of 7.5

The inventors have also demonstrated, for the nanobodies of the invention, a specific labeling of the cell bodies of the hippocampus, of the entorhinal cortex and of the temporal cortex in patients suffering from Alzheimer's disease.

Consequently, in one embodiment, the nanobodies of the invention also bind to the paired helical filaments and/or the straight filaments.

The term "paired helical filaments" denotes filaments paired in a helix comprising at least 10, at least 12, at least 20, preferably at least 40 Tau units, in particular at least 50 or at least 60 Tau units. Normally, these filaments can be observed by electron microscopy and have a diameter of from 8 to 20 nanometers, for example 10 to 20 nm and a helix pitch of approximately 80 nm, for example 70 up to 90 nm.

The term "straight filaments" means filaments which are not paired in a helix and which comprise at least 10, at least 12, at least 20, preferably at least 40 Tau units, in particular at least 50 or at least 60 Tau units. Normally, these filaments can be observed by electron microscopy and have a diameter of approximately 10 nanometers, for example from 8 to 17 nm, in particular from 9 to 12 nm, for example 10 nm.

The paired helical filaments and the straight filaments which make up the NFDs are not soluble.

In another embodiment, the nanobodies of the invention do not substantially interact with the polymerized amyloid beta 1-42 protein.

In one embodiment, the nanobodies do not substantially interact with the Tau protein in monomeric form.

A nanobody "does not substantially interact" with a protein, for example the polymerized amyloid beta 1-42 protein or the Tau protein in monomeric form, when the affinities for the Tau protein in oligomer form and the affinity for the Tau protein in monomer form or the polymerized amyloid beta 1-42 protein are very different. In one example, the affinity for the Tau protein in monomeric form cannot be measured because the binding response is too weak. In another example, a nanobody does not substantially interact with the Tau protein in monomeric form or the polymerized amyloid beta 1-42 protein, when the binding reaction of the nanobody with Tau in monomer form is less than 5% of the binding response of the same nanobody with Tau in oligomer form under the same experimental conditions and at the same nanobody concentration. In practice, the concentration of the nanobody used can be the EC50 concentration or the concentration required to reach the saturation plateau.

For example, the affinity of the nanobodies of the invention for the Tau protein in monomeric form is >1200 nM, for example >1400 nM, >1600 nM, >1800 nM, in particular >1800 nM.

For example, the affinity of the nanobodies of the invention for the polymerized amyloid beta 1-42 protein is >5000 nM, for example >8000 nM, >9000 nM, >10 000 nM, in particular >10 000 nM.

The nanobodies of the invention have been sequenced:

```
the 2C5 nanobody has the amino acid sequence
                                        (SEQ ID NO: 9)
QVQLVQSGGGLVQAGGSLRLSCAASGRTFSSDTLAWFRQAPGKEREFVAS

ISPSGGVTYYEDSVKGRFTISRDNSKNTVLLQMNSLTPEDTAVYYCNRDP

KYGNTRYWGQGTQVTVSS, the S2T2M3_E6 nanobody has the amino acid sequence
                                       (SEQ ID NO: 10)
EVQLVESGGGLVQAGGSLRLSCAASGRTFSRYAMGWFRQAPGKEREF

VASISRSGGSTRYADAVKGRFTISRDNTNNTVYLLMNNLKPEDTAVYYC

TARRRISGTPQWHYWGQGTQVTVSS.
```

The CDRs of these two nanobodies have been more specifically sequenced and are the following:

```
              2C5
              CDR1:
                                        (SEQ ID NO: 3)
              GRTFSSDT

CDR2:
                                        (SEQ ID NO: 4)
              ISPSGGVT

CDR3:
                                        (SEQ ID NO: 5)
              NRDPKYGNTRY

S2T2M2_E6
              CDR1:
                                        (SEQ ID NO: 6)
              GRTFSRYA

CDR2:
                                        (SEQ ID NO: 7)
              ISRSGGST

CDR3:
                                        (SEQ ID NO: 8)
              TARRRISGTPQWHY.
```

As is well known to those skilled in the art, the combination of the CDR1, CDR2 and CDR3 is sufficient to define an antigen-binding site. It is also known by those skilled in the art that two nanobodies which recognize the same antigen compete for binding to this antigen.

Consequently, a subject of the invention relates to a nanobody directed against the Tau protein, said Tau protein being in pathological form, in particular in oligomer form, and said nanobody competing for binding to the Tau protein in oligomer form with a nanobody comprising the amino acid sequences
(i) GRTFSX$_1$X$_2$X$_3$ (SEQ ID No. 1) as CRD1 in which the amino acid X$_1$ is S or R, X$_2$ is D or Y and X$_3$ is T or A,
(ii) ISX$_1$SGGX$_2$T (SEQ ID No. 2) as CRD2 in which the amino acid X$_1$ is P or R and X$_2$ is S or V, and
(iii) NRDPKYGNTRY (SEQ ID No. 5) or TARRRISGT-PQWHY (SEQ ID No. 8) as CRD3.

The capacity of a candidate nanobody to compete for binding to the Tau protein, for example in oligomer form, with a nanobody comprising the CDRs of a 2C5 and/or S2T2ME_E6 nanobody as defined above (hereinafter a "reference" nanobody) can be easily verified, for example by competitive ELISA in which the antigen (namely the Tau protein in oligomer form) is bound to a solid support and two solutions containing the candidate nanobody and the reference nanobody, respectively, are added and the nanobodies will compete to bind to the antigen. The amount of reference nanobody bound to the antigen can then be measured and compared with the amount of reference nanobody bound to the antigen when it is measured against a negative control (solution for example devoid of candidate nanobody). An amount of reference nanobody bound in the presence of candidate nanobody that is decreased compared with the amount of reference nanobody bound in the presence of the negative control indicates that the candidate nanobody competes for binding to the Tau protein in oligomer form. Ideally, the reference nanobody can be labeled (for example by fluorescence) in order to facilitate the detection of the bound reference nanobodies. Repeated measurements can be carried out with successive dilutions of the candidate and/or reference nanobody.

In another subject of the invention, the invention relates to a nanobody directed against the Tau protein, said Tau protein being in pathological form, in particular in oligomer form and said nanobody competing for binding to the Tau protein in oligomer form with a nanobody chosen from a nanobody comprising:

a) the amino acid sequences (i) GRTFSSDT (SEQ ID No. 3) as CDR1, (ii) ISPSGGVT (SEQ ID No. 4) as CDR2 and (iii) NRDPKYGNTRY (SEQ ID No. 5) as CDR3; or b) the amino acid sequences (i) GRTFSRYA (SEQ ID No. 6) as CDR1, (ii) ISRSGGST (SEQ ID No. 7) as CDR2 and (iii) TARRRISGTPQWHY (SEQ ID No. 8) as CDR3.

A subject of the present invention relates to a nanobody directed against the Tau protein comprising the amino acid sequences (i) GRTFSX$_1$X$_2$X$_3$ (SEQ ID No. 1) as CDR1 in which the amino acid X$_1$ is S or R, X$_2$ is D or Y and X$_3$ is T or A,
(ii) ISX$_1$SGGX$_2$T (SEQ ID No. 2) as CDR2 in which the amino acid X$_1$ is P or R and X$_2$ is S or V, and
(iii) NRDPKYGNTRY (SEQ ID No. 5) or TARRRISGTPQWHY (SEQ ID No. 8) as CDR3.

The invention also relates to a nanobody directed against the Tau protein comprising:

a) the amino acid sequences (i) GRTFSSDT (SEQ ID No. 3) as CDR1, (ii) ISPSGGVT (SEQ ID No. 4) as CDR2 and (iii) NRDPKYGNTRY (SEQ ID No. 5) as CDR3; or b) the amino acid sequences (i) GRTFSRYA (SEQ ID No. 6) as CDR1, (ii) ISRSGGST (SEQ ID No. 7) as CDR2 and (iii) TARRRISGTPQWHY (SEQ ID No. 8) as CDR3; or a functionally conservative variant of the nanobody defined in a) or b) comprising a conservative substitution of one or two amino acids in respectively one, two or three of the sequences SEQ ID No. 3, SEQ ID No. 4 and SEQ ID No. 5, or SEQ ID No. 6, SEQ ID No. 7 and SEQ ID No. 8.

In one preferred embodiment, this Tau protein is in oligomer form and optionally in fiber form.

The inventors have also sequenced the "framework" (FR) regions of the 2C5 and S2T2M2_E6 nanobodies. The corresponding sequences are the following:

```
2C5
FR1 region:
                               (SEQ ID NO: 11)
QVQLVQSGGGLVQAGGSLRLSCAAS FR2 region:
                               (SEQ ID NO: 12)
LAWFRQAPGKEREFVAS FR3 region:
                               (SEQ ID NO: 13)
YYEDSVKGRFTISRDNSKNTVLLQMNSLTPEDTAVYYC FR4 region:
                               (SEQ ID NO: 14)
WGQGTQVTVSS S2T2M2_E6
FR1 region:
                               (SEQ ID NO: 15)
EVQLVESGGGLVQAGGSLRLSCAAS FR2 region:
                               (SEQ ID NO: 16)
MGWFRQAPGKEREFVAS FR3 region:
                               (SEQ ID NO: 17)
RYADAVKGRFTISRDSTNNTVYLLMNNLKPEDTAVYYC FR4 region:
                               (SEQ ID NO: 18)
WGQGTQVTVSS.
```

In one particular embodiment, the invention relates to a nanobody directed against the Tau protein, said Tau protein being in pathological form, in particular in oligomer form, and said nanobody competing for binding to the Tau protein in oligomer form with a nanobody chosen from a nanobody comprising an amino acid sequence selected from the group consisting of the amino acid sequences SEQ ID No. 9 and SEQ ID No. 10.

In one particular embodiment, the invention relates to a nanobody comprising or consisting of the series of sequences FR1-CDR1-FR2-CDR2-FR3-CDR3-FR4 as defined above of one of the nanobodies identified by the inventors.

Preferably, the nanobody according to the invention is thus a nanobody comprising or consisting of an amino acid sequence selected from the group consisting of the amino acid sequences SEQ ID No. 9 and SEQ ID No. 10 or a functionally conservative variant thereof comprising a conservative substitution of one or two amino acids in one, two or three of the CDRs included respectively in the amino acid sequence SEQ ID No. 9 or SEQ ID No. 10. The functionally conservative variant as defined above may also comprise one or more substitutions, in particular one or more conservative substitutions in the regions respectively of the amino acid sequences SEQ ID No. 9 or SEQ ID No. 10 which are not CDRs, such as the "framework" regions, in particular the "framework" regions defined above. More preferably, the nanobody according to the invention is a nanobody comprising or consisting of an amino acid sequence selected from the group consisting of the amino acid sequences SEQ ID No. 9 and SEQ ID No. 10. Most preferably, the nanobody according to the invention is a nanobody comprising or consisting of the amino acid sequence SEQ ID No. 9.

In the context of the invention, the expression "functionally conservative variant" refers to variants in which a given amino acid in a nanobody according to the invention is replaced without impairing the overall conformation and the function of the nanobody, including replacement of one amino acid with another having similar properties (for example polarity, hydrogen bonding potential, acidity, basicity, hydrophobicity, presence of an aromatic group etc.). The amino acids having similar properties are well known to those skilled in the art. For example, arginine, histidine and lysine are hydrophilic-basic amino acids and can be interchangeable. Similarly isoleucine, a hydrophobic amino acid, can be replaced by leucine, methionine or valine. Such changes should have little or no effect on the apparent molecular weight or the isoelectric point of the nanobody. A natural amino acid can be replaced by an unnatural amino acid, such as an amino acid in D configuration, or a beta or gamma amino acid.

Examples of conservative substitutions are given in table 1 below.

TABLE 1

| Conservative substitutions I | |
|---|---|
| Side chain characteristic | Amino acid |
| Non-polar | GAPILV |
| Uncharged polar | CSTMNQ |
| Charged polar | DEKR |
| Aromatic | HFWY |
| Other | NQDE |

Alternatively, the conservative amino acids can be grouped as described in Lehninger (1975, Biochemistry, 2$^{nd}$ Edition, Worth Publishers, Inc. New York, N.Y., p. 71-77), as shown in table 2 below.

TABLE 2

Conservative substitutions II

| Side chain characteristic | | Amino acid |
|---|---|---|
| Non-polar | Aliphatic | ALIVP |
| | Aromatic | FW |
| | Containing sulfur | M |
| | Boundary | G |
| Uncharged polar | Hydroxyl | STY |
| | Amides | NQ |
| | Sulfhydryl | C |
| | Boundary | G |
| Positively charged (basic) | | KRH |
| Negative charged (acidic) | | DE |

According to another alternative, examples of conservative substitutions are given in table 3 below.

TABLE 3

Conservative substitutions III

| Original residue | Substitution example |
|---|---|
| A | VLI |
| R | KQN |
| N | QHKR |
| D | E |
| C | S |
| G | N |
| E | D |
| H | NQKR |
| I | LVMAF |
| L | IVMAF |
| K | RQN |
| M | LFI |
| F | LVIA |
| P | G |
| S | T |
| T | S |
| W | Y |
| Y | WFTS |
| V | ILMFA |

These functionally conservative variants retain the capacity to bind the Tau protein, in particular the Tau protein in oligomer form and optionally in fiber form. Preferentially, these functionally conservative variants have a binding affinity with Tau, in particular with Tau in oligomer form and optionally in fiber form, that is equal or increased compared with the corresponding nanobody.

As those skilled in the art know the amino acid sequence of the nanobody of interest, they are capable of producing the nanobodies according to the invention, in particular the 2C5 and S2T2M2_E6 nanobodies defined above, by conventional polypeptide production techniques. For example, they can be synthesized using the well-known solid-phase synthesis method (Merrifield (1962) *Proc. Soc. Ex. Boil.* 21: 412; Merrifield (1963) *J. Am. Chem. Soc.* 85: 2149; Tam et al. (1983) *J. Am. Chem. Soc.* 105: 6442), preferably using a commercially available peptide synthesis instrument (such as the one made by Applied Biosystems, Foster City, Calif.) and by following the manufacturer's instructions.

Alternatively, the nanobodies according to the invention can be synthesized by recombinant DNA techniques well known to those skilled in the art (Maniatis et al. (1982) Molecular Cloning: a laboratory manual, Cold Spring Harbor Laboratories, NY, 51-54 and 412-430). For example, they can be obtained as DNA expression products after incorporation of the DNA sequences encoding the polypeptide of interest into expression vectors and introduction of these vectors into the appropriate prokaryotic or eukaryotic hosts that will express the polypeptide of interest, from which they can then be isolated using techniques well known to those skilled in the art. As is well known to those skilled in the art, when a protein is synthesized by recombinant DNA techniques, it is generally synthesized linked to a tag that facilitates its purification. Such tags are well known to those skilled in the art and include, for example, hexahistidine (6His), glutathione S-transferase (GST), the myc tag or influenza virus hemagglutinin (HA). Preferably, the nanobodies according to the invention comprise a myc and/or hexahistidine tag. Consequently, a subject of the invention also consists of a nanobody comprising or consisting of the amino acid sequence chosen from the group consisting of the sequences SEQ ID No. 9 and SEQ ID No. 10, also comprising, at their C-terminal or N-terminal end, preferably at their C-terminal end, a myc and/or six histidine residues tag, more preferably a myc and six histidine residues tag. As is well known to those skilled in the art, when a protein is linked to a tag that facilitates its purification, such a protein comprises, between the native sequence and this tag, a sequence which allows enzymatic cleavage between the protein and this tag. A nanobody comprising or consisting of the amino acid sequence chosen from the group consisting of the sequences SEQ ID No. 19 and SEQ ID No. 20 is therefore also part of the invention.

Another subject of the invention relates to a nucleic acid comprising a nucleic sequence encoding the nanobody according to the present invention.

In one particular embodiment, the nucleic acid according to the invention comprises or consists of a nucleic sequence encoding a nanobody defined by one of the amino acid sequences SEQ ID No. 9 or SEQ ID No. 10. Preferably, the nucleic acid according to the invention comprises or consists of a nucleic sequence encoding the nanobody defined by the amino acid sequence SEQ ID No. 9.

Typically, said nucleic acid is a DNA or RNA molecule, which can be included in any appropriate vector, such as a plasmid, a cosmid, an episome, an artificial chromosome, a phage or a viral vector.

The terms "vector", "cloning vector" and "expression vector" mean the carrier by which the DNA or RNA sequence can be introduced into the host cell, in such a way as to transform the host and to promote the expression (e.g. transcription and translation) of the sequence introduced.

Consequently, another subject of the invention relates to a vector comprising a nucleic acid according to the invention.

Such vectors can comprise regulatory elements, such as a promoter, an activator, a terminator, etc., for causing or directing the expression of the polypeptide. Examples of promoters and activators used in expression vectors for animal cells include the SV40 early promoter and activator (Mizukami et al. (1987) *J. Biochem.* 101: 1307-1310), the Moloney mouse leukemia virus LTR promoter and activator, the immunoglobulin chain promoter (Mason et al. (1985) *Cell* 41: 479-487) and activator (Gillies et al. (1983) *Cell* 33: 717-728), etc.

Any expression vector for animal cells can be used. Examples of appropriate vectors include pAGE107 (Miyaji et al. (1990) *Cytotechnology* 3: 133-140), pAGE103 (Miaukami et al. (1987) *J. Biochem.* 101: 1307-1310), pHSG274 (Brady et al. (1984) *Gene* 27: 223-232), pKCR (O'Hare et al. (1981) *Proc. Natl. Acad. Sci. USA* 78: 1527-1531), pSG1 beta d2-4 (Miyaji et al. (1990) *Cytotechnology* 3: 133-140), etc.

Other examples of plasmids include replicating plasmids comprising an origin of replication, or integrating plasmids, such as for example pUC, pcDNA, pBR, etc.

Other examples of viral vectors include adenoviral, retroviral, herpes virus and AAV vectors. Such recombinant viruses can be produced by techniques well known to those skilled in the art, such as by transfection of packaging cells or by transient transfection with helper plasmids or viruses. Typical examples of virus packaging cells include PA317 cells, PsiCRIP cells, GPenv+ cells, 293 cells, etc. Detailed protocols for producing such replication-deficient recombinant viruses can be found for example in applications WO 95/14785, WO 96/22378, U.S. Pat. Nos. 5,882,887, 6,013,516, 4,861,719, 5,278,056 and WO 94/19478.

Another subject of the present invention relates to a cell that has been transfected, transduced or transformed with a nucleic acid and/or a vector according to the invention.

The term "transformation" means the introduction of a "foreign" (i.e. extrinsic or extracellular) gene or DNA or RNA sequence into a host cell, so that the host cell will express the gene or the sequence introduced so as to produce the substance of interest, typically a protein encoded by the gene or the sequence introduced. A host cell which receives and expresses the DNA or RNA introduced has been "transformed".

The nucleic acids according to the invention can be used to produce a nanobody according to the invention in an appropriate expression system. The term "expression system" means a host cell and a vector compatible under appropriate conditions, e.g. for the expression of a protein encoded by the foreign DNA carried by the vector and introduced into the host cell.

Conventional expression systems include *Escherichia coli* host cells and plasmid vectors, insect host cells and Baculovirus vectors, and mammalian host cells and their vectors. Other examples of host cells include prokaryotic cells (such as bacteria) and eukaryotic cells (such as yeast cells, mammalian cells, insect cells, plant cells, etc.). Specific examples include *Escherichia coli, Kluyveromyces* or *Saccharomyces* yeasts, mammalian cell lines (e.g. Vero cells, CHO cells, 3T3 cells, COS cells, etc.) and also primary or established mammalian cell cultures (e.g. produced from lymphoblasts, fibroblasts, epithelial cells, nerve cells, adipocytes, etc.). Examples also include mouse SP2/0-Ag14 cells (ATCC CRL1581), mouse P3X63-Ag8.653 cells (ATCC CRL1580), CHO cells in which a dihydrofolate reductase gene is defective, rat YB2/3HL.P2.G11.16Ag.20 cells (ATCC CRL1662), etc.

The present invention also relates to a method for producing a recombinant host cell expressing a nanobody according to the invention, said method comprising the steps consisting in:
 (i) introducing, in vitro or ex vivo, a nucleic acid as described above into a competent host cell,
 (ii) culturing, in vitro or ex vivo, the recombinant host cell obtained, and
 (iii) optionally selecting the cells which express and/or secrete said nanobody. Such recombinant host cells can be used for the production of nanobodies according to the invention.

The nanobodies according to the invention can be produced by any technique known to those skilled in the art, such as for example any chemical, biological, genetic or enzymatic technique, alone or in combination.

In particular, the invention also relates to a method for producing a nanobody according to the invention, said method comprising the steps consisting in:
 (i) culturing a transduced or transfected or transformed cell according to the invention under conditions suitable for allowing the expression of said nanobody, and
 (ii) recovering the nanobody expressed.

The nanobodies according to the invention can be suitably separated from the culture medium by conventional immunoglobulin purification procedures, such as for example protein A-sepharose, hydroxyapatite chromatography, gel electrophoresis, affinity dialysis or chromatography.

Labeled Nanobodies

The nanobodies according to the invention are particularly useful for medical imaging. In this context, it is particularly advantageous to have nanobodies linked to a detectable marker. The present inventors have shown that the 2C5 and S2T2M3_E6, in particular 2C5, nanobodies retain their properties when they are linked to a detectable marker.

The present invention thus also relates to a nanobody as defined above, bound to a detectable marker.

The term "nanobody bound to a detectable marker" is intended to mean herein that the detectable marker is directly or indirectly bound to the nanobody, for example via a cleavable or non-cleavable linker peptide, or is incorporated into the nanobody. The detectable marker can in particular be bound to the nanobody by substitution (for example by substituting an H with an I at the level of the tyrosine residues), by complexing or by chelation.

The term "detectable marker" is intended to mean herein a compound which produces a detectable signal. When it is linked to a tracer, it makes it possible to monitor what becomes of the tracer in the body. The detectable marker can be an MRI contrast agent, a scintigraphy contrast agent, an X-ray imaging contrast agent, an ultrasound contrast agent, an optical imaging contrast agent. Examples of detectable markers include radioelements, fluorophores such as fluorescein, Alexa or cyanine; chemiluminescent compounds such as luminol; bioluminescent compounds such as luciferase or alkaline phosphatase; and contrast agents such as nanoparticles or gadolinium. The choice of the suitable detectable marker, which depends on the detection system used, is within the scope of those skilled in the art. By way of example, when the detection system is MRI, the detectable marker is preferably an iron oxide nanoparticle or gadolinium; when the detection system is fluorescence imaging, the detectable marker is preferably fluorescein, Alexa or cyanine; when the detection system is chemiluminescence imaging, the detectable marker is preferably luminol; when the detection system is bioluminescence imaging, the detectable marker is preferably luciferase or alkaline phosphatase; when the detection system is nuclear imaging, the detectable marker is preferably a radioelement such as gallium ($^{68}$Ga) for PET imaging, or technetium 99m ($^{99m}$Tc) for SPECT imaging.

Preferably, the detectable marker is a radioelement. Examples of radioelements, which are more particularly used in nuclear imaging techniques, include technetium 99m ($^{99m}$Tc), iodine 123 ($^{123}$I), iodine 125 ($^{125}$I), fluorine 18 ($^{18}$F), gallium 68 ($^{68}$Ga), and any other radioelement that can be used in human beings. Consequently, preferably, the radioelement is chosen from the group consisting of $^{99m}$Tc, $^{123}$I, $^{125}$I, $^{18}$F and $^{68}$Ga. Most preferably, the radioelement is $^{99m}$Tc or $^{68}$Ga, more preferably $^{99m}$Tc.

Use as Contrast Agent

The inventors have demonstrated that the 2C5 nanobody allows specific labeling of the cell bodies of the hippocampus, of the entorhinal cortex and of the temporal cortex in patients suffering from Alzheimer's disease and in a pure tauopathy. The inventors have thus demonstrated that the nanobodies of the invention, in particular 2C5, constitute tracers specific for the pathological forms of the Tau protein, in particular for the early pathological forms of Tau, for example Tau in oligomer form and optionally in fiber form, and allow its detection by imaging.

The invention thus provides a nanobody as defined above, for use thereof as a contrast agent in medical imaging, in particular noninvasive, in vivo medical imaging.

It also relates to the use of a nanobody as defined above, for the production of a contrast agent that is of use for medical imaging, in particular noninvasive, in vivo medical imaging.

The term "contrast agent" is intended to mean herein a substance or a composition which, when administered to the body, makes it possible to detectably label organs or structures (tissue, cell, receptor) which, without contrast agent, are barely visible or are invisible in medical imaging. By extension, the expression "contrast agent" is used to denote a tracer linked to a marker as defined above.

In the context of the invention, the "imaging methods" refer to methods which make it possible to visualize the inside of a body or organs of a body. Examples of imaging methods include invasive techniques such as intravascular ultrasound, and noninvasive techniques such as magnetic resonance imaging, X-ray imaging, ultrasound, optical imaging, or nuclear medicine such as scintigraphy, in particular single-photon emission computed tomography (SPECT) and positron emission tomography (PET). Preferably, the imaging method according to the invention is scintigraphy, in particular SPECT or PET scintigraphy.

Scintigraphy is based on the administration (generally intravenously) of a contrast agent, also called radiopharmaceutical, consisting of a tracer labeled with a radioelement. The specific localization of this contrast agent in the body is then determined by detecting the gamma or beta rays emitted.

Single-photon emission computed tomography and positron emission tomography are tomographic nuclear medical imaging techniques based on scintigraphy and which make it possible to produce three-dimensional images and reconstructions of the organs and of their metabolism by means of a set of cameras which revolve around the patient.

The present invention also relates to a medical imaging method, in particular a noninvasive, in vivo medical imaging method, in which a nanobody as defined above is administered to a patient. The medical imaging method according to the invention can also comprise the steps of detecting the binding or the absence of binding of the nanobody in areas of the patient's body and of visualizing the areas of the patient's body in which the binding of a nanobody can be detected.

In the context of the invention, a "patient" denotes a human or nonhuman mammal, such as a rodent (rat, mouse, rabbit), a primate (chimpanzee), a feline (cat), or a canine (dog). Preferably, the individual is a human being.

In one particular embodiment, the term "patient" denotes a human being who presents symptoms associated with a tauopathy. Depending on the tauopathy, these symptoms may for example be Parkinsons' syndrome, axial dystonia, alien hand phenomenon, or cognitive problems of the patient.

Any administration method, known to those skilled the art, can be used to administer the nanobody according to the invention to the patient. In particular, the nanobody can be administered for example orally, by inhalation or parenterally (in particular by intravenous injection). When the parenteral route is chosen, the nanobody can be in the form of injectable solutions and suspensions, packaged in vials or bottles. The parenteral administration forms are conventionally obtained by mixing the nanobody according to the invention with buffers, stabilizers, preservatives, solubilizing agents, isotonic agents and suspending agents. According to known techniques, these mixtures can be sterilized and packaged in the form of intravenous injections. Those skilled in the art can for example use phosphate-salt-based buffers as buffers. Examples of suspending agents include methylcellulose, acacia and sodium carboxymethylcellulose. Examples of stabilizers include sodium sulfite and sodium metasulfite, and examples of preservatives include sodium p-hydroxybenzoate, sorbic acid, cresol and chlorocresol.

The amount of nanobody administered naturally depends on the route of administration, on the height and/or on the weight of the patient, and on the detection technique used.

In the context of the invention, the term "area of the body" refers to a given region of the organism. It may for example be an organ, a part of an organ or a tissue, such as the brain, in particular the hippocampus, the entorhinal cortex or the temporal cortex.

In one particular embodiment, the nanobody according to the invention is used as a contrast agent in medical imaging for visualizing the Tau protein in pathological form, in particular for visualizing Tau in a form chosen from oligomers, fibers, paired helical filaments and straight filaments, preferably oligomers and fibers, even more preferably oligomers, in a patient.

In one embodiment, the nanobody according to the invention is used as a contrast agent in medical imaging for visualizing neurofibrillary degenerations (NFDs) in a patient.

In one example, the cortical distribution and the number of the, for example, NFDs correlate with memory problems in the patient suffering for example from AD.

Diagnostic Use

The appearance of the pathological forms of the Tau protein, as defined above, is a marker for a tauopathy. In addition, the detection of the pathological forms of Tau, in particular of the early pathological forms, such as the Tau protein in oligomer and optionally fiber forms, makes it possible to identify the presence of the toxic forms involved in the propagation or development of one of the tauopathies. The identification of the pathological forms, in particular of the early pathological forms, such as Tau in oligomer and optionally fiber form, thus constitutes the characterization of a tauopathy and/or the identification of the beginning of a tauopathy. Furthermore, the possibility of monitoring, by imaging, the evolution, that is to say the progression or the regression, of a previously identified pathological form of Tau represents a mode for evaluating the efficacy of a therapeutic treatment in a patient in whom a tauopathy has been diagnosed.

The invention thus also relates to a nanobody as defined above, for use thereof in methods of diagnosis or of prognosis.

The term "diagnostic method" or "diagnosis" is intended to mean herein a method which makes it possible to determine whether an individual is suffering from a pathological condition.

The term "prognostic method" or "prognosis" is intended to mean herein a method which makes it possible to determine whether an individual risks developing a pathological condition.

Preferably, the nanobody as defined above is used for the diagnosis or prognosis of a tauopathy.

The tauopathies are as defined above. Preferably, the nanobody according to the invention is used for the diagnosis or prognosis of Alzheimer's disease.

The presence, for example, of Tau in oligomer form exposes the subject to a risk of developing a tauopathy, in particular Alzheimer's disease. The nanobody according to the invention can thus be used for detecting a risk of occurrence of a tauopathy, in particular Alzheimer's disease, in a patient.

The term "risk of occurrence" is intended to mean herein the probability that an individual will develop a pathological condition.

The present invention also relates to a method for the diagnosis of a tauopathy and/or for the detection of a risk of occurrence of a tauopathy in a patient, said method comprising the steps consisting in administering a nanobody as defined above to said patient and in detecting said nanobody in the body of said patient, the detection of a preferential localization of said nanobody in the brain being indicative of a tauopathy and/or of a risk of occurrence of a tauopathy.

In one embodiment, said method also comprises the steps consisting of administering an amyloid plaque marker to said patient and in detecting said amyloid plaque marker in the body of said patient, the detection of a preferential localization of said nanobody and of said amyloid plaque marker in the brain being indicative of a tauopathy and/or of a risk of occurrence of a tauopathy, in particular of Alzheimer's disease.

Consequently, the present invention also relates to a method for the diagnosis of a tauopathy, in particular Alzheimer's disease, and/or for the detection of a risk of occurrence of a tauopathy, in particular of Alzheimer's disease, in a patient, said method comprising the steps consisting in:

i) administering a nanobody according to the invention to said patient and in detecting said nanobody in the body of said patient, and ii) administering an amyloid plaque marker to said patient and in detecting said amyloid plaque marker in the body of said patient, the detection of a preferential localization of said nanobody and of said amyloid plaque marker in the brain being indicative of a tauopathy, in particular of Alzheimer's disease and/or of a risk of occurrence of a tauopathy, in particular of Alzheimer's disease.

In one embodiment, these methods for the diagnosis of a tauopathy are in vivo methods.

The term "amyloid plaque marker" is intended to mean tracers which are bound to a detectable marker that specifically binds to amyloid plaques, and which can be used as a contrast agent in noninvasive, in vivo medical imaging. Amyloid plaque markers are, for example, $^{18}F$ tracers such as 18F-florbetapir, 18F-forbetaben, 18F-flutemetanol and 18F-AZD4694-marque.

The region of the brain which, depending on the particular tauopathies, is affected by the presence of the pathological forms of Tau is described in the prior art and is therefore known to those skilled in the art. The localization in the brain of neurofibrillary degenerations or of other pathological forms of Tau and possibly of amyloid plaques is described for several tauopathies, for example in Catafau, A M and Bullich, S (Clin Transl Imaging. 2015; 3 (1): 39-55. Epub 2015 Jan. 21) or in Tranchant, C. (médicine/sciences A1997; 13: 989-97).

The term "preferential localization" is intended to mean that the amount of nanobody detected in the brain, in particular for example in the cell bodies of the hippocampus, frontal neocortex, entorhinal cortex and temporal cortex, is greater than the background noise which corresponds to a nonspecific location of the nanobody in the body.

For example, progressive supranuclear paralysis is characterized by the presence of NFD in the brain stem and in the frontal neocortex.

In another example, corticobasal degeneration is characterized by the presence of NFD in the parietal cortex.

In another example, Alzheimer's disease is characterized by the presence of NFD in the entorhinal cortical structures.

The invention also relates to the nanobody according to the invention, for use thereof for the therapeutic monitoring of a tauopathy in a subject in whom a tauopathy has been diagnosed.

It also relates to the use of the nanobody according to the invention for producing a contrast agent that is of use for the therapeutic monitoring of a tauopathy in a subject in whom a tauopathy has been diagnosed.

The term "therapeutic monitoring" is intended to mean herein the observation of the subject's response to the treatment administered to said subject. The therapeutic effect of a treatment is generally associated with a slowing down or an inhibition of the progression of a disease, or a reversion of the disease, or of one or more symptoms associated with this disease. Conversely, an absence of therapeutic effect can result in stability, or even acceleration, of the progression of the disease or one or more of the symptoms thereof. For example, if a tauopathy has been diagnosed because of the presence of the pathological forms of Tau, the therapeutic monitoring can be carried out by observing the disappearance, regression, maintenance or growth of the pathological forms of Tau. Thus, the use according to the invention may comprise the steps consisting in:

a) administering a nanobody as defined above to a subject in whom a pathological form of Tau has been detected;

b) detecting the binding of the nanobody on said pathological form of Tau;

c) repeating steps a) and b) before and after administering a treatment to said subject;

an absence of or a decrease in the binding of the nanobody on said pathological form of Tau being indicative of a treatment having a therapeutic effect.

The "pathological form of Tau" is as defined in the "tauopathy" section above.

Preferably, the treatment is a treatment of a tauopathy and comprises for example the use of Tau aggregation inhibitors. In another example, the treatment of a tauopathy comprises the use of nanobodies of the invention.

Use as a Medicament

Recently, it has been shown that the pathological forms of Tau, for example extracellular toxic forms, represent the toxic forms of Tau (Usenovic et al., 2015) involved in the propagation (Goedert et al., 2014) of tauopathies such as AD in the brain, by gradual contamination of the neurons. Consequently, targeting the toxic forms of Tau in order to inhibit the aggregation thereof and thus the formation of paired helical filaments (PHFs) and straight filaments (SFs) is a promising treatment for tauopathies, in particular for Alzheimer's disease.

Consequently, the invention also relates to the use of a nanobody as defined above, for producing a medicament, in particular a medicament intended for the treatment of a tauopathy. A method of treatment comprising the administration of a therapeutically effective amount of the nanobody as defined above to a patient in need thereof is also part of the present invention.

The use of an anti-Tau nanobody thus makes it possible to inhibit the progression of Tau aggregation.

The term "treatment" of a tauopathy is intended to mean "therapeutic treatment" (or curative treatment) of a tauopathy, which includes the slowing down or inhibiting of the progression of a tauopathy. It is also intended to mean the "prophylactic treatment" of a tauopathy, which includes in particular the prevention of NFD formations.

The term "prevention" is intended to mean preventing or delaying the occurrence of or decreasing the intensity of the clinical or biochemical manifestations associated with the tauopathy.

Those skilled in the art know, by virtue of their general knowledge, how to determine the clinical or biochemical manifestations which are associated with a given tauopathy and which are capable of being improved (treatment) or else prevented, delayed or decreased in intensity (prevention). In the context of tauopathies, a biological parameter of interest may be the presence and the localization of Tau in pathological form, in particular Tau in early pathological form, such as the Tau protein in oligomer form and optionally Tau in fiber form.

The invention relates more particularly to the nanobody as defined above, for use thereof for the treatment of a tauopathy and/or in the prevention of a tauopathy, preferably for the treatment and/or prevention of Alzheimer's disease.

The invention also relates to the use of a nanobody as defined above, for producing a medicament intended for the treatment of a tauopathy and/or for the prevention of a tauopathy in a patient liable to present a tauopathy.

The invention also relates to a method for treating a tauopathy and/or for preventing a tauopathy in a patient in need thereof, comprising the administration of a therapeutically effective amount of a nanobody as defined above to a patient in need thereof.

Preferentially, the nanobody according to the invention is used to treat the pathological forms of Tau, in particular the early pathological forms, such as the oligomer forms of Tau and eventually the fiber forms of Tau.

The nanobody according to the invention can be administered for example orally, by inhalation, parenterally (in particular by intravenous injection), in a suitable form. When the parenteral route is envisioned, the nanobody may be in the form of injectable solutes and suspensions packaged in vials or bottles. The forms for parenteral administration are obtained conventionally by mixing the nanobody with buffers, stabilizers, preserving agents, solubilizing agents, isotonic agents and suspending agents. In accordance with known techniques, these mixtures are subsequently sterilized and then packaged in the form of intravenous injections. By way of buffer, those skilled in the art may use buffers based on organic phosphate salts. Examples of suspending agents encompass methylcellulose, hydroxyethylcellulose, hydroxypropylcellulose, acacia and sodium carboxymethylcellulose. In addition, stabilizers that are of use according to the invention are sodium sulfite and sodium metasulfite, while mention may be made of sodium p-hydroxybenzoate, sorbic acid, cresol and chlorocresol as preservatives.

The amount of nanobody administered naturally depends on the method of administration, on the height and/or the weight of the patient, and on the nature of the cytotoxic agent with which it may be combined.

The present invention also relates to a pharmaceutical composition comprising a nanobody as defined above in combination with a pharmaceutically acceptable carrier.

The term "pharmaceutically" or "pharmaceutically acceptable" refers to molecular entities and compositions which do not produce side reactions, allergic reactions or reactions that are otherwise bothersome when they are administered to a mammal, in particular a human being.

In the context of the invention, the expression "pharmaceutically acceptable carrier" includes any solvent, dispersion medium, coating, antibacterial or antifungal agent, isotonic agent or absorption-delaying agent, and the like. The use of such media and agents for pharmaceutically active substances is well known to those skilled in the art. With the exception of the case where a conventional medium or agent is incompatible with the active ingredient, the use thereof in the pharmaceutical compositions is envisioned. Additional active ingredients may also be incorporated into the compositions.

Use for Detecting Tau In Vitro

The present invention also relates to the use of a nanobody as defined above, for the in vitro detection of the Tau protein in oligomer form in a sample.

The term "sample" is intended to mean herein a portion of a larger element. Preferably, the sample is a substance of biological origin. Examples of biological samples include, but are not limited to, portions of organs or of tissues such as the brain, in particular the hippocampus, the entorhinal cortex or temporal cortex, the blood, in particular cerebral blood, the cerebrospinal fluid. Preferably, a sample in the context of the invention relates to a brain sample.

The present invention will be illustrated in greater detail by the figures, the sequences and the example below.

BRIEF DESCRIPTION OF THE SEQUENCES

SEQ ID NO. 1 shows the consensus CDR1 amino acid sequence of the nanobodies of the invention in which the amino acid $X_1$ is S or R, $X_2$ is D or Y and $X_3$ is T or A.

SEQ ID NO. 2 shows the consensus CDR2 amino acid sequence of the nanobodies of the invention in which the amino acid $X_1$ is P or R and $X_2$ is S or V.

SEQ ID NO. 3 shows the CDR1 amino acid sequence of the 2C5 nanobody.

SEQ ID NO. 4 shows the CDR2 amino acid sequence of the 2C5 nanobody.

SEQ ID NO. 5 shows the CDR3 amino acid sequence of the 2C5 nanobody.

SEQ ID NO. 6 shows the CDR1 amino acid sequence of the S2T2M3_E6 nanobody.

SEQ ID NO. 7 shows the CDR2 amino acid sequence of the S2T2M3_E6 nanobody.

SEQ ID NO. 8 shows the CDR3 amino acid sequence of the S2T2M3_E6 nanobody.

SEQ ID NO. 9 shows the amino acid sequence of the variable region of the 2C5 nanobody.

SEQ ID NO. 10 shows the amino acid sequence of the variable region of the S2T2M3_E6 nanobody.

SEQ ID NO. 11 shows the amino acid sequence of the FR1 region of the 2C5 nanobody.

SEQ ID NO. 12 shows the amino acid sequence of the FR2 region of the 2C5 nanobody.

SEQ ID NO. 13 shows the amino acid sequence of the FR3 region of the 2C5 nanobody.

SEQ ID NO. 14 shows the amino acid sequence of the FR4 region of the 2C5 nanobody.

SEQ ID NO. 15 shows the amino acid sequence of the FR1 region of the S2T2M2_E6 nanobody.

SEQ ID NO. 16 shows the amino acid sequence of the FR2 region of the S2T2M2_E6 nanobody.

SEQ ID NO. 17 shows the amino acid sequence of the FR3 region of the S2T2M2_E6 nanobody.

SEQ ID NO. 18 shows the amino acid sequence of the FR4 region of the S2T2M2_E6 nanobody.

SEQ ID NO. 19 shows the amino acid sequence of the variable region of the 2C5 nanobody with a myc and six histidine residues tag.

SEQ ID NO. 20 shows the amino acid sequence of the variable region of the S2T2M3_E6 nanobody with a myc and six histidine residues tag.

SEQ ID NO. 21 shows the amino acid sequence of the 2N4R isoform of the Tau protein, also called Tau-F, with 441 amino acids.

SEQ ID NO. 22 shows the amino acid sequence of the 1N4R isoform of the Tau protein, also called Tau-E, with 412 amino acids.

SEQ ID NO. 23 shows the amino acid sequence of the 0N4R isoform of the Tau protein, also called Tau-D, with 383 amino acids.

SEQ ID NO. 24 shows the amino acid sequence of the 2N3R isoform of the Tau protein, also called Tau-C, with 410 amino acids.

SEQ ID NO. 25 shows the amino acid sequence of the 1N3R isoform of the Tau protein, also called Tau-B, with 381 amino acids.

SEQ ID NO. 26 shows the amino acid sequence of the 0N3R isoform of the Tau protein, also called Fetal-Tau, with 352 amino acids.

SEQ ID NO. 27 shows the amino acid sequence of the truncated Tau protein consisting of the 3R region of the Tau protein.

EXAMPLE

Figure 1:
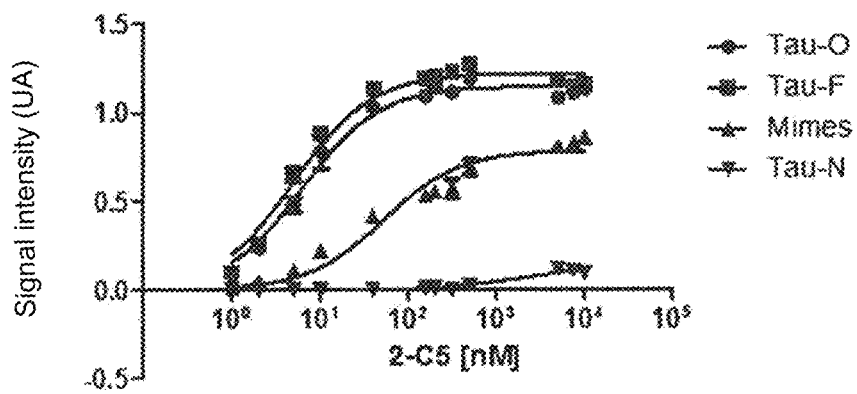
FIG. 1: Graph which shows the results of the ELISA assays and thus curves of affinity of the 2C5 nanobody for Tau-O (Tau oligomers), Tau-F (Tau fibers), Mimetics (the R3 region of polymerized Tau) and Tau-N (native taus).

1. Nanobody Generation:
(1) Preparation of the Antigens Required for the Camelid Immunization:

The cDNA (htau40) encoding the longest isoform of Tau (441aa—45.8 kDa) was cloned into a plasmid pRK172, downstream of the T7 RNA polymerase promoter. *Escherichia coli* BL21 bacteria (obtained from Goedert, M. et al., *Neuron*, 3(4): 519-526 (1989)) (bacteria supplied by the team of Prof. Baulieu, INSERM, Paris) were transformed with the recombinant plasmids. The protein was purified by two steps of FPLC (Fast Protein Liquid Chromatography): (1) using an $SO_4^-$-loaded cation exchange column (HiTrap SP-XL, Thermoscientific) then (2) using exclusion chromatography (HiTrap Sepharose HP column—Amersham Biosciences). In order to obtain preparations enriched with various polymerized forms of tau (oligomer and fibers) mimicking in vivo Tau fibrillation, the method of Haase et al. (*Journal of Neurochemistry*, 88(6): 1509-1520, 2004) modified by Flach et al. (*Journal of Biological Chemistry*, 2012, (287)52: 43223-43233) was used. The fibrillation of Tau (40 μM) is carried out at 37° C. in 20 mM MOPS (3-(N-morpholino)propanesulfonic acid) buffer, pH 7, in the presence of heparin (10 μM) and of $NaN_3$ (4%), for a final volume of 1.5 mL [21] [14]. The fibrillation is analyzed as described above. The fibrillation is stopped by freezing the samples at −80° C. after 48 hours and 72 h. The duration of the polymerization process is adapted to the production (a) of oligomers and (b) of fibers. In parallel, a peptide covering the R3 region of the Tau repeat motifs was synthesized and polymerized in a similar manner. In particular, the fibrillation of R3 (0.4 μM) is carried out at 37° C. in 50 mM PBS (phosphate buffered saline) buffer, at pH 7, in the presence of heparin (0.4 μM) and of $NaN_3$ (4%), for a final volume of 1.5 ml. The fibrillation is stopped by freezing the samples at −80° C. after typically 72 hours, so as to obtain truncated Tau (R3) in fiber form.

(2) Llama Immunization:
A llama was immunized under the same conditions with a mixture consisting of Tau oligomers and fibers and also of R3 polymers ((a), (b), (c)). Three successive injections were carried out on days 0, 9, 18. The blood samples are taken on days 28 and 42. The blood bags are centrifuged on a Ficoll gradient in order to separate and isolate the lymphocytes, and the total RNAs are extracted.

(3) Nanobody Production and Screening: They Comprise Several Steps:

Amplification and production of the llama lymphocyte mRNAs.

Generation of a phage library expressing the nanobodies of the previously immunized dromedary.

Selection, by ELISA assays and by FACS, of phages expressing anti-tau-oligomer nanobodies.

Sequencing of the selected clones and identification of distinct clones.

Determination of the sequences of the Nbs.

Construction and production of the mRNA fragment encoding an Nb comprising a C-term Myc and histidine tag.

Insertion into bacteria and bulk production of the Nb.

2. In Vitro Characterization of the Nanobodies:

The nanobodies were characterized for their affinity and their specificity through two steps:

a) ELISA assays I: with the starting antigens, that is to say preparation enriched with tau oligomers, preparation enriched with tau fibers, polymerized R3, and also the native tau protein and amyloid beta peptide fibers (produced from commercially available peptide). The affinity constants of the nanobodies were determined for each of these immunogens.

b) Immunohistochemistry: on paraffin sections of tissues originating from human anatomical pathology (collaboration with the Department of Mental Health and Psychiatry in Geneva). These sections cover various more or less severe tauopathy cases.

c)

Figure 5:
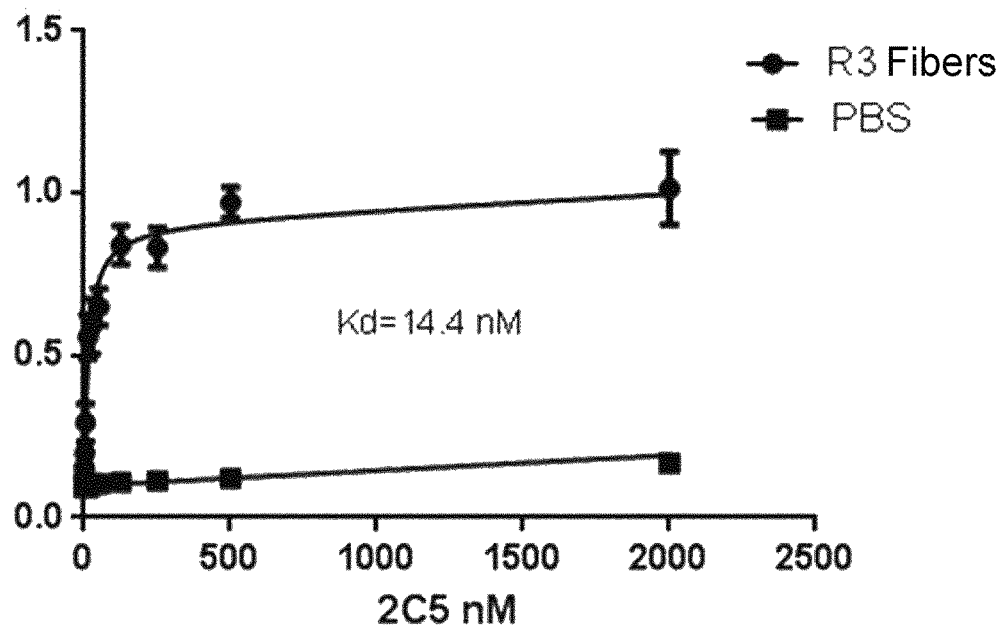
FIG. 5: Graph which shows the results of the ELISA assays and thus curves of affinity of the 2C5 nanobody (without radiolabeling) for polymers of the R3 sequence of the Tau protein.
Figure 6:
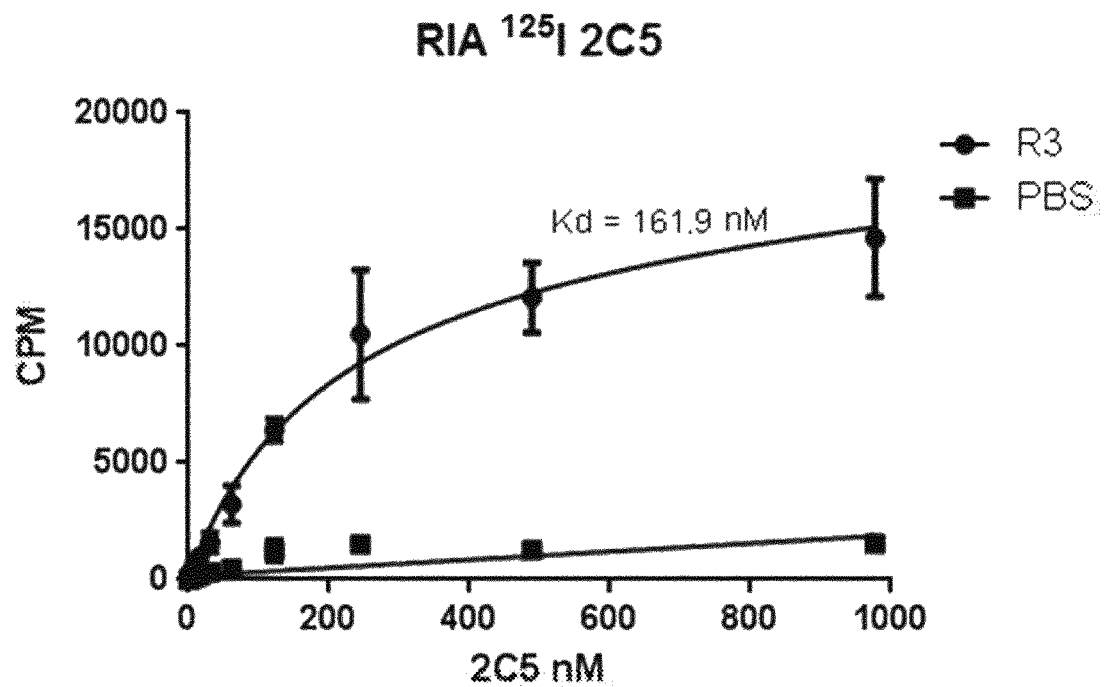
FIG. 6: Graph which shows the results of the ELISA assays and thus of the curves of affinity of the 2C5 nanobody (radiolabeled with iodine 125) for polymers of the R3 sequence of the Tau protein.

The tissue sections were deparaffinized and then treated as floating sections after permeabilization in PBS-0.2% Triton buffer and unmasking of the antigen by means of a commercial unmasking solution (Vector H-3300). The primary antibody (Nb) is applied at various concentrations 20 nM) overnight at 4° C. After rinsing, a rabbit anti-histidine antibody is applied for 1 h at ambient temperature and then a goat anti-rabbit third antibody is finally applied, for 1 h, after rinsing. The visualization is carried out by means of two incubation steps in the presence of avidin-biotin complex (Vector ABC kit) and then diaminobenzidine (Vector ABC kit). Control sections are systematically prepared in the absence of the first antibody (Nb). The sections are mounted on a slide and counterstained with hematoxilin.

d) ELISA assays II: the 2C5 nanobody was radiolabeled with iodine 125. The affinity assays for polymers of the R3 sequence of the Tau protein are carried out by ELISA, in a phosphate buffered saline buffer (NaCl, 137 mM; KCl, 2.7 mM, $Na_2HPO_4$, 10 mM, $KH_2PO_4$, 1.8 mM), 1% BSA; pH=7.5. The ELISAs are carried out before (FIG. 5) and after (FIG. 6) radiolabeling. It is noted that, after radiolabeling, the ligand retains good affinity for its target (FIG. 6).

3. Results:

Several camelid antibodies with a single variable domain (Nbs), directed specifically against early pathological forms of the Tau protein (oligomers and fibers) of low molecular weight (15 kDa) were produced: 2C5 (VHH), S2T2M3 E6 (VHH).

Figure 2:
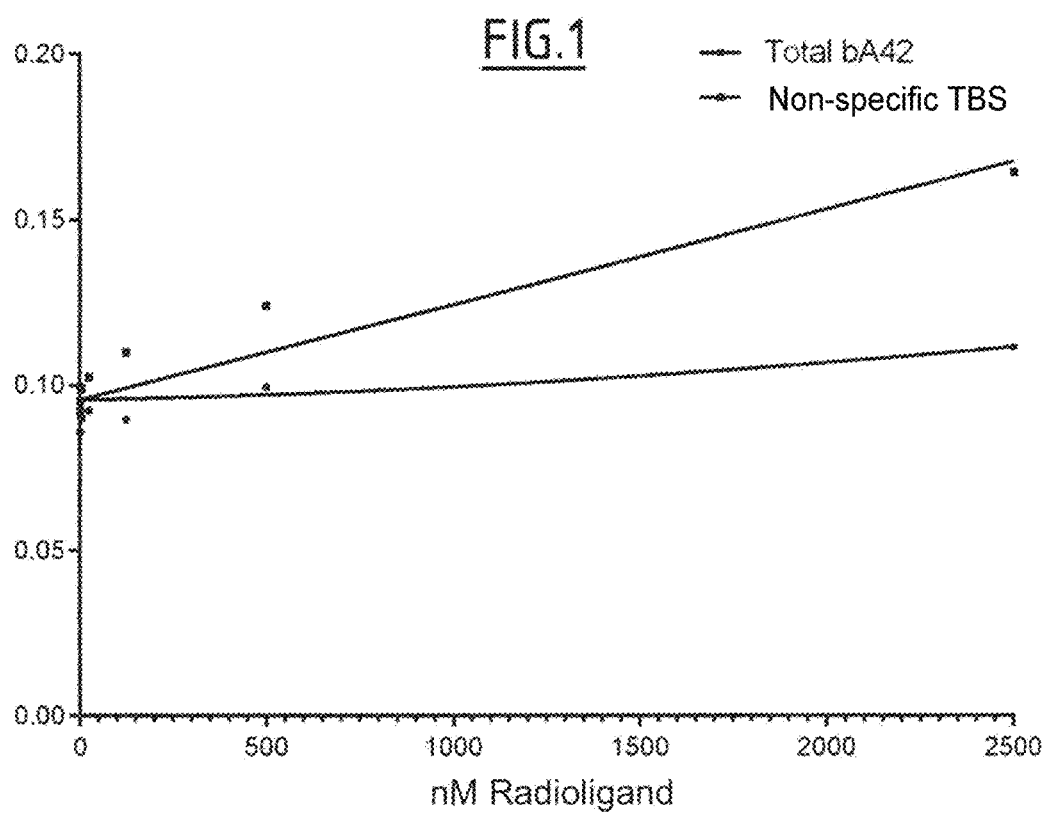
FIG. 2: Graph which shows the absence of affinity for the polymerized Abeta1-42 amyloid peptide.

The 2C5 Nb was sequenced and characterized as VHH and characterized in vitro. It exhibits respective affinities (Kd) of 5 nM, 6 nM and 50 nM for the oligomers, the fibers and polymerized truncated forms of Tau. This Nb binds neither to the native Tau protein (Kd>1800 nM) nor to the amyloid beta peptide fibers (Kd>10 000 nM). (FIGS. 1 and 2).

Figures 3, 4:
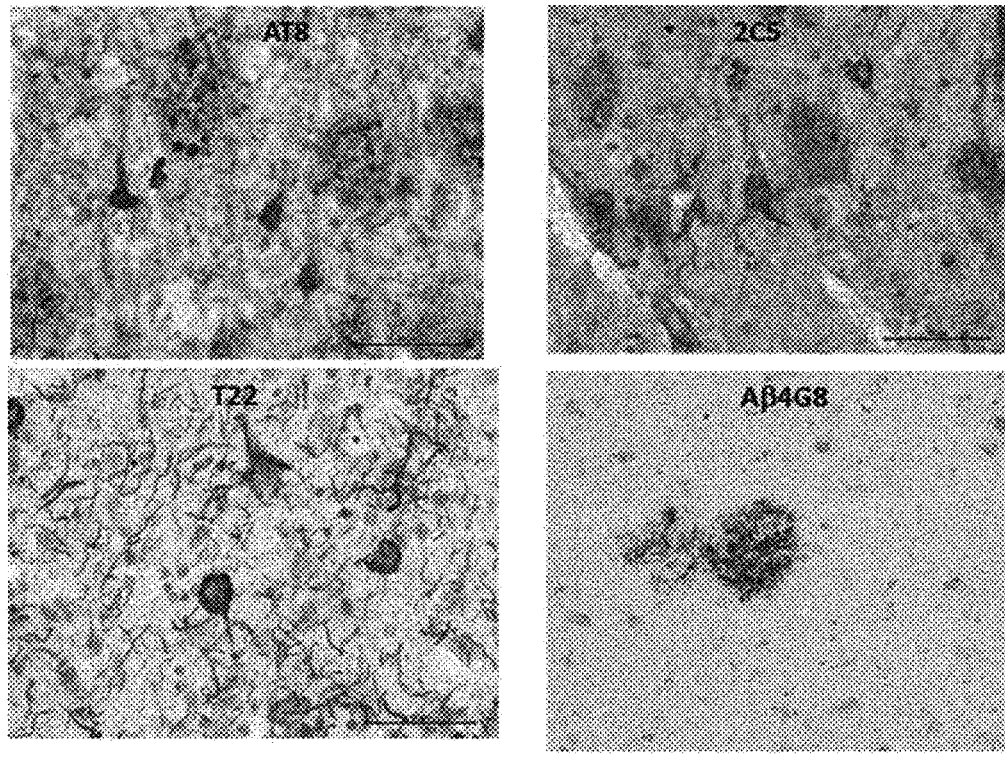
FIG. 3: Comparative immunohistochemistry on sections of temporal cortex of a case of AD; A) AT8 is a: monoclonal antibody directed against the PHFs phosphorylated at Ser202 and Thr205; B) 2C5 is the nanobody of the invention directed against Tau in oligomer form; C) T22 is a monoclonal antibody directed against the tau oligomers; D) Ab4G8 is a monoclonal antibody directed against the aggregated forms of amyloid beta peptide.
FIG. 4: Alignment of the variable sequences of the nanobodies of the invention, 2C5_VHH (SEQ ID NO:9) and S2T2M3_E6_VHH (SEQ ID NO:10).

This Nb was tested by immunohistochemistry on sections of human brains originating from anatomical pathology (Alzheimer's of different grade and tauopathy). It demonstrates specific labeling of the cell bodies of the hippocampus, of the entorhinal cortex and of the temporal cortex in patients suffering from Alzheimer's disease and in one case of dementia with pure tauopathy (table 4, FIG. 3).

The technecium 99m radiolabeling of this SdAbs was successfully carried out.

The S2T2M3 E6 Nb was selected for its affinity for the low-molecular-weight tau polymers.

TABLE 4

Human anatomical pathology cases tested for 2C5

| Pathology type | Standard abbreviation | Age | Sex | Break Stage | CDR | MMS |
|---|---|---|---|---|---|---|
| Normal aging | C | ? | ? | 1 | ? | ? |
| AD | AD | ? | ? | 5 | ? | ? |
| AD | AD | 74 | F | 5 | na | 15/30 |
| AD | AD | 81 | F | 5 | na | 17/30 |
| Tangle only dementia | T | 73 | M | 4 | na | na |
| PSP/CBD | PSP/CBD | ? | ? | No | ? | ? |

The invention claimed is:

1. A nanobody directed against the Tau protein, said Tau protein being in oligomer form and said nanobody being devoid of a light chain, said nanobody comprising the amino acid sequences:
   (i) GRTFSX$_1$X$_2$X$_3$ (SEQ ID No. 1) as CDR1 in which the amino acid X$_1$ is S or R, X$_2$ is D or Y and X$_3$ is T or A,
   (ii) ISX$_1$SGGX$_2$T (SEQ ID No. 2) as CDR2 in which the amino acid X$_1$ is P or R and X$_2$ is S or V, and
   (iii) NRDPKYGNTRY (SEQ ID No. 5) or TARRRISGTPQWHY (SEQ ID No. 8) as CDR3.

2. The nanobody as claimed in claim 1, said nanobody competing for binding to the Tau protein in oligomer form with a nanobody comprising:
   a) the amino acid sequences (i) GRTFSSDT (SEQ ID No. 3) as CDR1, (ii) ISPSGGVT (SEQ ID No. 4) as CDR2 and (iii) NRDPKYGNTRY (SEQ ID No. 5) as CDR3; or
   b) the amino acid sequences (i) GRTFSRYA (SEQ ID No. 6) as CDR1, (ii) ISRSGGST (SEQ ID No. 7) as CDR2 and (iii) TARRRISGTPQWHY (SEQ ID No. 8) as CDR3.

3. The nanobody as claimed in claim 1, said nanobody comprising:
   a) the amino acid sequences (i) GRTFSSDT (SEQ ID No. 3) as CDR1, (ii) ISPSGGVT (SEQ ID No. 4) as CDR2 and (iii) NRDPKYGNTRY (SEQ ID No. 5) as CDR3; or
   b) the amino acid sequences (i) GRTFSRYA (SEQ ID No. 6) as CDR1, (ii) ISRSGGST (SEQ ID No. 7) as CDR2 and (iii) TARRRISGTPQWHY (SEQ ID No. 8) as CDR3.

4. The nanobody as claimed in claim 1, said nanobody comprising the amino acid sequences SEQ ID No. 9 or SEQ ID No. 10.

5. The nanobody as claimed in claim 4, said nanobody comprising an amino acid sequence consisting of SEQ ID No. 9.

6. The nanobody as claimed in claim 1, said nanobody being bound to a detectable marker.

7. The nanobody as claimed in claim 6, said detectable marker being a radioelement.

8. A pharmaceutical composition comprising the nanobody as claimed in claim 1 in combination with a pharmaceutically acceptable carrier.

9. A nucleic acid comprising a nucleic acid sequence encoding the nanobody as claimed in claim 1.

10. A vector comprising the nucleic acid as claimed in claim 9.

11. A cell comprising the nucleic acid as claimed in claim 9.

12. A method for producing a nanobody, said method comprising:
   (i) culturing the cell as claimed in claim 11, under conditions suitable for allowing the expression of said nanobody, and
   (ii) recovering the nanobody expressed.

13. A method of inhibiting progression of Tau aggregation comprising administering to a subject the nanobody as claimed in claim 1.

14. A method for noninvasive, in vivo medical imaging, comprising administering to a subject the nanobody as claimed in claim 1; and detecting binding or absence of binding of the nanobody in an area of the subject's body.

15. A method for diagnosis of a tauopathy comprising administering to a subject the nanobody as claimed in claim 1; detecting said nanobody in the subject's body; and diagnosing the subject as having a tauopathy or at risk of a tauopathy when the amount of said nanobody detected in the brain is greater than the background noise which corresponds to a nonspecific location of the nanobody in the body.

16. A method of in vitro detection of the Tau protein in oligomer form in a sample comprising contacting an in vitro sample with the nanobody as claimed in claim 1; and detecting the nanobody bound to Tau protein in oligomer form in the sample.

17. A method for producing a recombinant host cell expressing a nanobody, said method comprising:
   (i) introducing, in vitro or ex vivo, a nucleic acid comprising a nucleic sequence encoding the nanobody as claimed in claim 1 into a competent host cell,
   (ii) culturing, in vitro or ex vivo, the recombinant host cell obtained, and
   (iii) optionally selecting the cells which express and/or secrete said nanobody.

* * * * *